US012491305B2

(12) United States Patent
Shidham

(10) Patent No.: US 12,491,305 B2
(45) **Date of Patent: *Dec. 9, 2025**

(54) VASCULAR ACCESS CATHETER WITH PROTECTABLE INLINE NEEDLE AND ASSOCIATED METHOD OF USE THEREOF

(71) Applicant: Aadi Innovations LLC, Columbus, OH (US)

(72) Inventor: Aaditya Shidham, Columbus, OH (US)

(73) Assignee: Aadi Innovations LLC, Columbus, OH (US)

( * ) Notice: Subject to any disclaimer, the term of this patent is extended or adjusted under 35 U.S.C. 154(b) by 920 days.

This patent is subject to a terminal disclaimer.

(21) Appl. No.: 17/712,931

(22) Filed: Apr. 4, 2022

(65) Prior Publication Data

US 2022/0226613 A1 Jul. 21, 2022

Related U.S. Application Data

(63) Continuation-in-part of application No. 16/012,007, filed on Jun. 19, 2018, now Pat. No. 11,291,755.

(51) Int. Cl.

| | |
|---|---|
| ***A61M 1/36*** | (2006.01) |
| ***A61M 25/00*** | (2006.01) |
| ***A61M 25/06*** | (2006.01) |

(52) U.S. Cl.

CPC ...... *A61M 1/3661* (2014.02); *A61M 25/0097* (2013.01); *A61M 25/0606* (2013.01)

(58) Field of Classification Search

CPC .... A61M 1/3661; A61M 1/14; A61M 1/3655; A61M 5/32; A61M 5/321; A61M 5/3271;

(Continued)

(56) References Cited

U.S. PATENT DOCUMENTS 4,362,156 A * 12/1982 Feller, Jr. .......... A61M 25/0637 604/177
4,834,718 A 5/1989 McDonald (Continued)

FOREIGN PATENT DOCUMENTS

| | | | |
|---|---|---|---|
| CN | 202822325 | U | 9/2012 |
| CN | 204017014 | U | 12/2014 |
| EP | 2204211 | A2 | 7/2010 |

*Primary Examiner* — Philip R Wiest

(74) *Attorney, Agent, or Firm* — Standley Law Group LLP; Adam J. Smith; Kenny W. Pung

(57) ABSTRACT

Exemplary embodiments described herein are directed to a vascular access catheter device with an inline needle, the device having a needle portion that is linearly displaceable relative to a catheter portion, and vice versa, and to methods of performing blood transfer procedures using said device. Retraction of the needle portion relative to the catheter portion allows the catheter of the catheter portion to cover the needle tip during a blood transfer procedure, thereby preventing needle damage to a fistula/graft or peripheral vessel of a patient, as well as possible needle stick injuries to health care workers during removal/disposal of a used device. Because the needle still remains largely within the catheter after retraction, there is no risk of catheter collapse, kinking, etc., during use, which could compromise blood flow during a hemodialysis or other vascular access procedure.

20 Claims, 22 Drawing Sheets

(58) Field of Classification Search
CPC .......... A61M 25/0606; A61M 25/0618; A61M 25/0631; A61B 5/1513; A61B 5/15003; A61B 5/15019; A61B 5/15076; A61B 5/150641; A61B 5/158
See application file for complete search history.

(56) References Cited

U.S. PATENT DOCUMENTS

| | | | | |
|---|---|---|---|---|
| 4,952,207 | A | 8/1990 | Lemieux | |
| 5,011,475 | A | 4/1991 | Olson | |
| 5,041,097 | A | 8/1991 | Johnson | |
| 5,108,376 | A * | 4/1992 | Bonaldo | A61M 25/0631 604/110 |
| 5,407,431 | A | 4/1995 | Botich et al. | |
| 5,545,146 | A | 8/1996 | Ishak | |
| 5,800,400 | A | 9/1998 | Hogan | |
| 5,931,815 | A | 8/1999 | Liu | |
| 5,954,698 | A | 9/1999 | Pike | |
| 6,139,532 | A | 10/2000 | Howell et al. | |
| 6,206,851 | B1 | 3/2001 | Prosl | |
| 6,461,362 | B1 * | 10/2002 | Halseth | A61M 25/0631 600/576 |
| 6,736,798 | B2 | 5/2004 | Ohkubo et al. | |
| 6,972,002 | B2 | 12/2005 | Thorne | |
| 7,153,276 | B2 | 12/2006 | Barker et al. | |
| 7,322,963 | B2 | 1/2008 | Goh | |
| 7,335,187 | B2 | 2/2008 | Altman | |
| 7,413,560 | B2 * | 8/2008 | Chong | A61M 25/0637 604/164.08 |
| 7,556,617 | B2 * | 7/2009 | Voorhees, Jr. | A61M 25/0631 604/164.08 |
| 7,753,878 | B2 * | 7/2010 | Jones | A61M 25/0637 604/110 |
| 7,785,296 | B2 | 8/2010 | Muskatello et al. | |
| 7,951,115 | B2 | 5/2011 | Altman | |
| 8,257,322 | B2 | 9/2012 | Koehler et al. | |
| 8,591,473 | B2 | 11/2013 | Jones et al. | |
| 8,597,249 | B2 | 12/2013 | Woehr et al. | |
| 9,044,552 | B2 | 6/2015 | Schraga | |
| 9,375,552 | B2 | 6/2016 | Tremblay | |
| 11,291,755 | B2 * | 4/2022 | Shidham | A61M 1/14 |
| 2008/0319387 | A1 | 12/2008 | Amisar et al. | |

* cited by examiner

VASCULAR ACCESS CATHETER WITH PROTECTABLE INLINE NEEDLE AND ASSOCIATED METHOD OF USE THEREOF

CROSS-REFERENCE TO RELATED APPLICATIONS

This application is a continuation-in-part of U.S. application Ser. No. 16/012,007, filed on Jun. 19, 2018, which is hereby incorporated by reference as if fully recited herein.

TECHNICAL FIELD

Exemplary embodiments described herein are directed to a vascular access catheter with an inline needle that is protectable by sliding displacement of the needle relative to the catheter, or vice versa.

BACKGROUND

Worldwide there are currently about 2 million patients with End Stage Renal disease (ESRD). There were about 660,000 such patients in the United States as of 2013 according to the United States Renal Data System (USRDS). Out of those 660,000 ESRD patients, about 465,000 patients were receiving hemodialysis treatment, which is the process of removing extra fluids and toxins from the body and maintaining normal electrolyte levels by passing the patient's blood through a dialysis filter and subsequently returning the blood to the patient. Hemodialysis is typically performed in 3-4 hour sessions, three times per week.

Because hemodialysis involves extracting blood from the patient and returning the filtered blood to the patient, hemodialysis obviously requires repeated access to the arteriovenous system of the patient. A fistula or graft is commonly created in order to provide an effective vascular access point. An arteriovenous (AV) fistula is a surgically created direct connection of an artery to a vein, which becomes a permanent (but surgically reversible structure after a sufficient healing period). An AV graft, while similar to an AV fistula, employs a plastic tube to connect and artery to a vein. In either case, once the fistula/graft is ready to use, the fistula/graft provides the arteriovenous access required to remove and return a patient's blood during hemodialysis treatment. The proper function of a fistula/graft is critically important for most hemodialysis patients.

One of the most important steps in the hemodialysis process is cannulation of the fistula/graft. Two needles are typically inserted into a fistula/graft for arteriovenous access. One of the needles is used to direct blood from the patient through a connected tube to the dialysis filter of the dialysis machine, while the other needle is used to direct filtered blood from the dialysis machine through a connected tube back to the patient. Required blood flow through the needles may be on the order of 250-550 ml/min. To achieve this blood flow, the needles used are usually of large diameter (e.g., between 17 and 14 gauge).

In operation of most currently used hemodialysis needles, the skin of a patient is pierced by the tip of the dialysis needle, and the needle is further inserted until the tip also pierces the fistula/graft. Once the needle is properly placed in the fistula/graft, it is normally secured in place by taping it to the associated limb of the patient.

As should be obvious, the tip of a hemodialysis needle is sharp. Use of a typical hemodialysis needle generally results in the sharp tip of the needle floating in the fistula/graft. Consequently, any needle migration or movement of the limb of the patient in which the fistula/graft has been created, can cause the needle tip to damage the fistula/graft, such as by causing a counter puncture of the fistula/graft wall. Such a puncture can result in infiltration where blood leaks outside of the fistula/graft. Studies have reported an annual infiltration rate of about 5.2% of all hemodialysis treatments, which is a significant problem.

Because blood is typically flowing through the hemodialysis needles at rate of 250-550 ml/min, a significant amount of blood can accumulate in surrounding tissues and form a hematoma as a result of a counter puncture and associated infiltration. An infiltration can be very painful, and often times requires that the fistula/graft be allowed to heal before further use. Thus, a patient may either have to miss dialysis treatment for a period of time, or a temporary dialysis catheter may need to be placed in a central vein of the patient in order to permit continued dialysis until the fistula/graft heals. It is also possible that an infiltration can lead to permanent loss of use of the damaged fistula/graft.

It can be understood from the foregoing description that there is a heretofore unmet need for an improved device and method for providing hemodialysis arteriovenous access without fistula/graft damage. A similar need exists for providing peripheral vessel access without damage. Exemplary vascular access catheter devices described herein satisfy this need.

SUMMARY

Exemplary vascular access catheter device embodiments described and shown herein are designed to provide hemodialysis arteriovenous access without fistula/graft damage, and may also be used to access peripheral vessels in non-dialysis patients. Generally speaking, exemplary vascular access catheter device embodiments include a catheter with an inline needle, where the sharp tip of the needle is protectable by the catheter during use to prevent fistula/graft or peripheral vessel damage due to, for example, limb movement or needle migration. Exemplary vascular access catheter device embodiments may also function to prevent needle stick injuries to persons performing hemodialysis or other procedures, and may allow for parking of the catheter before final engagement, which permits minor adjustments to the catheter and the needle to obtain optimum blood flow.

Certain combined hemodialysis needle and catheter devices are known. In one such known device, a needle protrudes from a catheter portion of the device and is used to pierce a patient's skin so as to facilitate insertion of the needle tip and a portion of an overlying catheter into the vasculature (e.g., fistula/graft) of the patient. Once placed in the patient's fistula/graft, the needle portion is subsequently withdrawn by retracting a plunger to leave only the catheter inserted. Retracting the needle pulls it out of the catheter and into a housing portion of the device so as to prevent needle injury to the fistula/graft during use. However, since the needle is withdrawn completely from the catheter and into housing, the catheter alone is responsible for conducting blood flow during hemodialysis treatment. Unfortunately, because the catheter is typically thin-walled plastic tubing, it is often weak, which may lead to kinking and possible partial collapse due to high blood flow rate, thereby impairing the hemodialysis procedure.

Exemplary vascular access catheter device embodiments described and shown herein are single use devices designed to produce vascular access (i.e., fistula/graft or peripheral vessel access), and to connect to a dialysis machine via elongate tubing in the case of a hemodialysis application. An exemplary vascular access catheter device includes an inline needle that is concentrically located within a slidable catheter portion while protruding slightly therefrom during certain times. The sharp tip of the needle may be used to pierce a patient's skin and fistula/graft or peripheral vessel, whereafter a catheter tip of the slidable catheter portion will follow the needle tip into the fistula/graft or peripheral vessel and the needle portion may subsequently be slidably retracted so that the needle tip is covered by the catheter during use of the device. The catheter position relative to the needle position may be secured to ensure that the needle tip remains within the catheter once the needle has been fully retracted.

The catheter of an exemplary vascular access catheter device is thus placed without removing the needle, thereby maintaining the catheter and needle in communication with the patient's blood without a break in the (e.g., dialysis) blood flow path. The needle tip is also protected by the catheter during use of the device, which prevents fistula/graft/peripheral vessel injury and infiltration in patients and needle stick injuries to health care workers and other users of the device. Further, since the needle still resides within a majority of the catheter, issues such as kinking and partial collapse of the catheter are avoided, thereby preserving blood flow. Unlike known combination needle and catheter devices, exemplary vascular access catheter device embodiments do not require any special training prior to use.

An exemplary vascular access catheter device may include a needle portion having a needle that extends from a needle hub, and a catheter portion that is supported on the needle portion and includes a catheter that extends from a catheter hub. The needle may extend concentrically within the catheter such that a sharp tip of the needle protrudes from an open end of the catheter when the catheter portion is in a retracted position/needle portion is in an extended position. The catheter portion is slidable relative to the needle portion, and vice versa, such that the catheter or needle may be linearly displaced to selectively expose or cover the needle tip. Some exemplary embodiments of a vascular access catheter device may also include a body portion that is supported on the needle portion. The body portion may include a gripping structure that facilitates handling and use of the device. In other embodiments, a gripping structure may be associated with the needle portion of the device. An exemplary gripping structure may be provided in the form of extending wings or in other forms that also facilitate removable attachment of the device to a patient during use.

In one exemplary vascular access catheter device, the position of the catheter portion relative to the needle portion of the device may be maintained by a retention mechanism in the form of a detent element on the catheter hub and an associated annular groove on the needle hub, or vice versa.

In another exemplary vascular access catheter device, the position of the catheter portion relative to the needle portion of the device may be maintained by a retention mechanism in the form of a bolt that extends from the needle hub through a detent groove in the catheter hub.

In another exemplary vascular access catheter device, the position of the catheter portion relative to the needle portion of the device may be maintained by a retention mechanism in the form of a tab that extends from the needle hub through a detent groove in the catheter hub.

In another exemplary vascular access catheter device, the position of the catheter portion relative to the needle portion of the device may be maintained by a retention mechanism in the form of a pin or bolt that extends from the needle hub through a curved cam slot in the catheter hub. The cam slot may allow for parking of the catheter portion in an extended position before final engagement with a patient. adversarial In another exemplary vascular access catheter device, the position of the catheter portion relative to the needle portion of the device may be maintained by a retention mechanism in the form of a retention slot in the catheter hub that engages a gripping element of the needle portion when the catheter portion is extended. The retention slot may be designed to lock the catheter hub to the gripping element such that the catheter portion cannot be again retracted once fully extended.

In another exemplary vascular access catheter device, at least one position of the needle portion of the device relative to the catheter portion of the device may be maintained by a locking mechanism in the form of at least one tab that extends from the catheter portion into at least one corresponding receiving slot in at least one gripping element associated with the needle portion.

An exemplary vascular access catheter device may include a seal between the needle and the catheter to prevent the leakage of blood from the device during use.

In at least one exemplary vascular access catheter device, at least a portion of the needle and catheter portion of the device may be enclosed within a safety cap when not in use.

The catheter hub and needle hub of an exemplary vascular access catheter device may be manufactured from a transparent or semi-transparent material to permit viewing of the flow of blood passing through the device during use.

Other aspects and features of the inventive concept will become apparent to those skilled in the art upon review of the following detailed description of exemplary embodiments along with the accompanying drawing figures.

BRIEF DESCRIPTION OF THE DRAWINGS

In the following descriptions of the drawings and exemplary embodiments, like reference numerals across the several views refer to identical or equivalent features, and.

DETAILED DESCRIPTION OF THE EXEMPLARY EMBODIMENTS

Figure 1A:
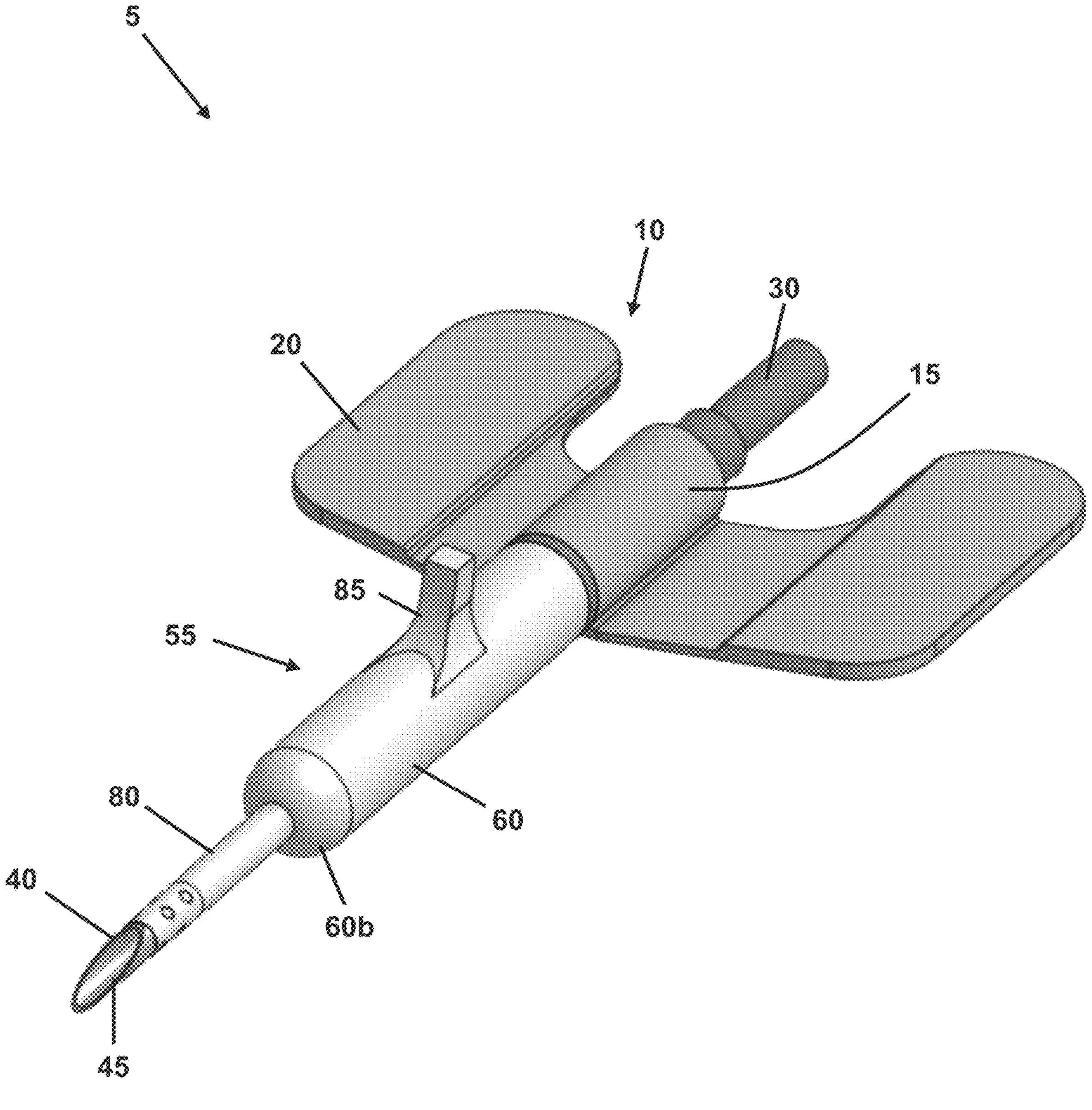
FIG. 1A is a top perspective view of one exemplary embodiment of a catheter device according to the general inventive concept, with a catheter portion thereof in a retracted position that exposes a needle tip.
Figure 1B:
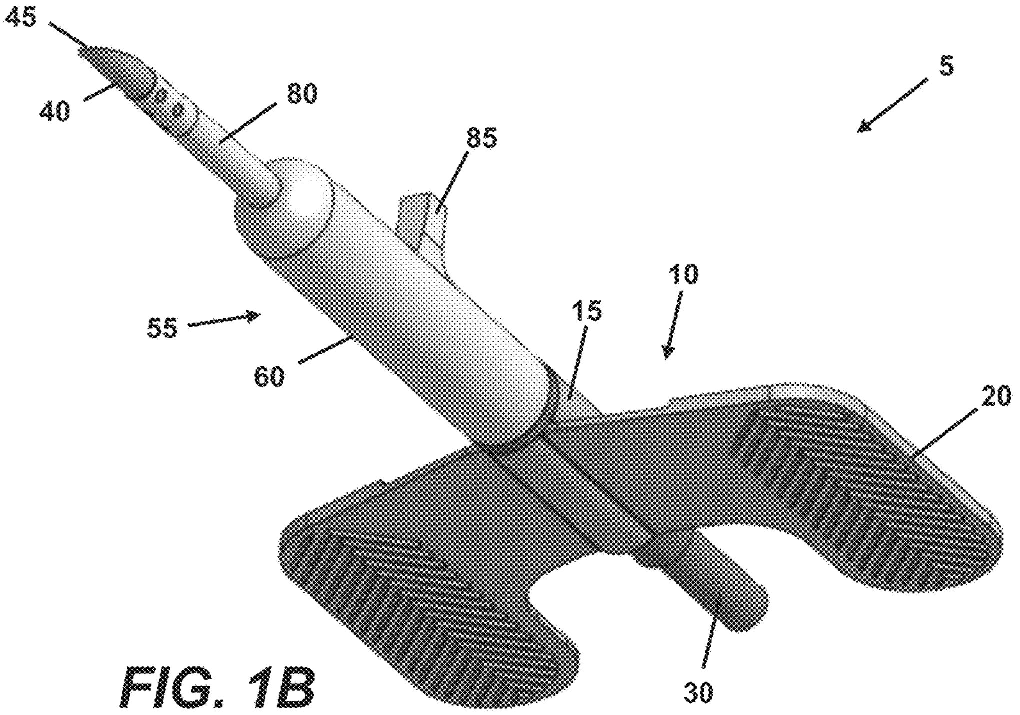
FIG. 1B is a bottom perspective view of the catheter device of FIG. 1A.
Figure 1C:
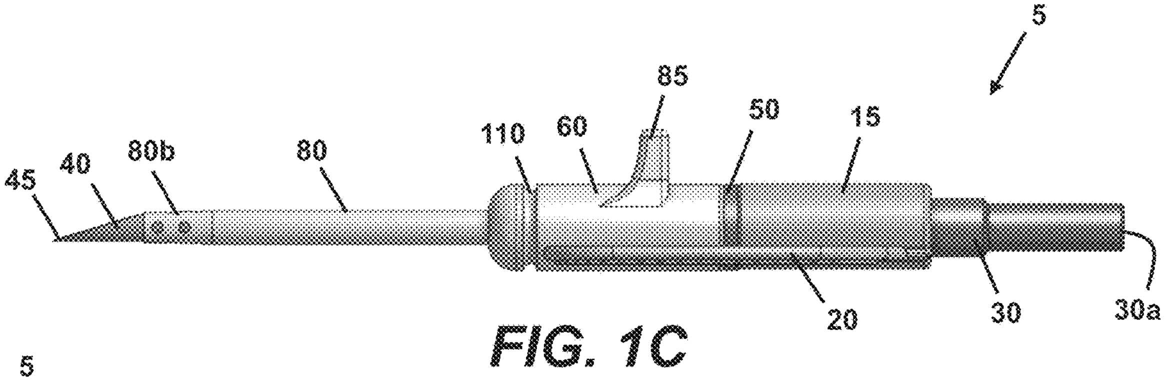
FIG. 1C is a side view of the catheter device of FIG. 1A.

One exemplary embodiment of a vascular access catheter device (e.g., arteriovenous catheter device) 5 is illustrated in FIGS. 1A-2D. As may be observed, the device 5 includes a needle portion 25 on which is supported a body 10 and a catheter portion 55. The body 10 includes a central mounting sleeve 15 and a pair of wing-like gripping portions 20 that extend substantially laterally outward from opposite sides of the central mounting sleeve. While the overall body 10 may be of various shapes, in this exemplary embodiment the gripping portions 20 of the body are shaped as shown to facilitate gripping and manipulation of the device 10 by a user and taping of the device to a limb of a patient after fistula/graft or peripheral vessel access. Similarly, the central mounting sleeve 15 is cylindrical and hollow in the exemplary embodiment so as to slide over a correspondingly-shaped hub of a needle portion (see below), the mounting sleeve may be of other shapes as needed to cooperate with a given needle hub. The body 10 may be constructed from various different materials, with plastic (e.g., fluoroplastic) being a particularly good material.

It also may be observed that the catheter device 5 includes a needle portion 25 and a catheter portion 55. The needle portion 25 includes an elongate needle hub 30 having a proximal end 30*a* and a distal end 30*b*. An axial bore 35 passes through the needle hub to provide, among other things, a pathway for blood flow during a hemodialysis or other vascular access procedure. Tubing (not shown) may be coupled to the proximal end 30*a* of the needle hub for connecting the catheter device 5 to a hemodialysis machine, as would be understood by one of skill in the art.

A needle 40 of the needle portion 25 has a proximal end 40*a* thereof inserted sufficiently far into the bore 35 in the distal end 30*b* of the needle hub 30 to securely retain the needle. The proximal end 40*a* of the needle 40 may be retained in the needle hub 30 by a press fit or a similar interaction between the components. Alternatively, or in conjunction with such other techniques, an adhesive or other affixation mechanism may be used to further secure the needle 40 in the needle hub 30. A distal, free end 40*b*, of the needle is provided with a sharp point 45 for the purpose of piercing the skin of a patient and subsequently accessing the patient's fistula/graft or peripheral vessel. The specific needle gauge, needle construction, etc., may vary in keeping with accepted practices understood in the art.

The inside diameter of the central mounting sleeve 15 of the body 10 is dimensioned to pass over a portion of the needle hub 30. As shown, the needle hub 30 may include a protruding collar 50 or similar element that is designed and located to abut a distal face of the central mounting sleeve 15 and to thereby act as a stop for the body 10 when the body is properly installed on the needle hub 30. The collar may also act as a rear (retraction) stop for the catheter portion 55, as is described in more detail below.

The central mounting sleeve 15 of the body 10 may be retained on the needle hub 30 of the needle portion 25 by any of the same techniques mentioned above relative to securing the needle 40 in the bore 35 of the needle hub. Other techniques known to those of skill in the art may also be employed. Threaded engagement of the central mounting sleeve 15 and the needle hub 30 is also possible.

Figure 1D:
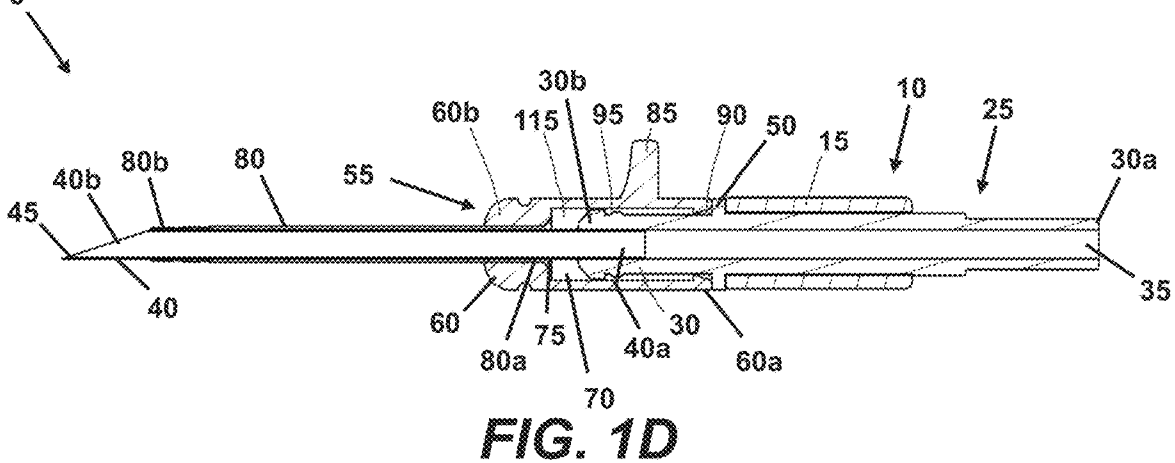
FIG. 1D is a cross-sectional view of the catheter device of FIG. 1C.

As shown particularly clearly in the section view of FIG. 1D, the collar 50 is located such that some length of the needle hub 30 extends distally therefrom. As is described below, this distally-extending portion of the needle hub 30 of this exemplary catheter device 5 is designed to retain and act as a guide for sliding movement of the catheter portion 55 of the device.

In similar fashion to the needle portion 25, the catheter portion 55 includes a catheter hub 60 with proximal and distal ends 60*a*, 60*b*. The size and shape of the catheter hub 60 is selected so that the catheter hub will cooperate with the needle hub 30. More specifically, the catheter hub 60 is of substantially cylindrical shape, and includes a first central bore 70 at the proximal end 60*a* that is dimensioned to permit the catheter hub to slide over the portion of the needle hub 30 that extends distally of the collar 50. This arrangement allows the catheter portion 55 of the catheter device 5 to be supported on the needle portion 25 and to slide linearly relative to the needle hub 30 (and the body 10). A second central bore 75 extends inward from the distal end 60*b* of the catheter hub 60 and opens into the proximally-located needle hub receiving bore 70.

The catheter portion 55 further includes a hollow catheter 80 that extends longitudinally outward from the distal end 60*b* of the catheter hub 60. In this exemplary embodiment, the catheter 80 has an open proximal end 80*a* that is inserted sufficiently far into the second bore 75 in the catheter hub 60 to securely retain the catheter. The proximal end 80*a* of the catheter 80 may be retained in the catheter hub 60 by any of the needle retention techniques mentioned above or by any other acceptable technique known to one of skill in the art. In other embodiments, the catheter 80 may be an integrally molded part of the catheter hub 60. A distal, free open end 80*b*, of the catheter 80 may be tapered and/or may include any other features that may facilitate entry of the free end of the catheter into the fistula/graft or peripheral vessel of the patient subsequent to initial access by the needle 40 and/or may facilitate blood flow during a hemodialysis or other vascular access procedure.

The inside diameter of the catheter is preferably similar in dimension to the outside diameter of the needle 40 so as to produce a close tolerance but sliding fit between the catheter 80 and the needle 40 when the catheter hub 60 is installed over the needle hub 30. Nonetheless, a seal 115 may be placed at or near the entry point of the second bore 75 into the first bore 70 to prevent possible blood leakage between the needle 40 and the catheter 80 during use of the catheter device 5. As with the needle 40, the specific construction of the catheter 80 may otherwise vary in keeping with accepted practices understood in the art. For example, the catheter may be constructed from a fluoroplastic material.

From the foregoing description and corresponding FIGS. 1A-2D, it should be understood that when the body 10 and catheter portion 55 are properly assembled to the needle portion 25, as explained above, the needle hub 30 is substantially concentrically located within the catheter hub 60, the needle 40 is substantially concentrically located within the catheter 80, and the catheter hub 60 and attached catheter 80 are together linearly slidable relative to the needle hub 30 and the attached needle 40. As shown in the drawing figures, a gripping element 85 or similar feature may be provided on the catheter hub 60 to facilitate sliding of the catheter portion 55 by a user of the device 5.

FIGS. 1A-1D show the catheter portion 55 in a retracted position, which results in the needle tip 45 and perhaps some additional length of the needle 40 protruding from the open distal end 80*b* of the catheter. This is the proper position in which the catheter portion 55 should reside during initial piercing of the patient's skin and accessing of the underlying fistula/graft or peripheral vessel using the needle 40 of the device 5.

With the tip of the needle 40 and the catheter 80 residing in the patient's fistula/graft or peripheral vessel, the catheter portion 55 may then be placed in an extended position (see FIGS. 2A-2D) by sliding the catheter portion linearly and in a distal direction along the needle hub 30 such that the sharp tip 45 of the needle becomes covered by the distal end 80*b* of the catheter 80. A distal catheter hub hard stop or a similar mechanism (see below) may be used to ensure proper linear positioning and possibly position retention of the catheter portion. With the needle 40 and the catheter 80 properly located in the fistula/graft or peripheral vessel of the patient, the catheter device 5 may be secured against movement, such as but not limited to by taping the gripping portions 20 of the body 10 to the limb of the patient.

As should be readily obvious to one of skill in the art, placing the catheter 80 of the exemplary catheter device 5 into the fistula/graft or peripheral vessel and over the needle tip 45 as described above serves to prevent the needle tip from damaging the fistula/graft or peripheral vessel and also, therefore, prevents infiltration and related hematoma problems. And unlike known devices, the needle 40 of the exemplary device 5 remains largely within the catheter 80 during a hemodialysis or other vascular access procedure, thereby substantially eliminating any chance that the catheter may collapse, kink, etc., and interfere with blood flow or cause damage on its own.

As described above, the catheter portion 55 has a retracted position where the catheter 80 is kept from interfering with use of the needle to initially access the fistula/graft or peripheral vessel of a patient. Likewise, the catheter portion 55 also has an extended position where the open distal end 80*b* of the catheter 80 will extend at least equal with if not beyond the tip 45 of the needle and into the fistula/graft or peripheral vessel currently accessed by the needle. Consequently, it is preferable to provide a mechanism by which it can be ensured that the catheter portion 55 is properly in the retracted position or the extended position, and by which either position can be maintained once selected.

In the case of the exemplary catheter device 5 of FIGS. 1A-2D, position retention is provided by a detent mechanism formed through interaction of certain elements of the catheter hub and the needle hub. This relationship may be reversed in other embodiments.

Figure 2A:
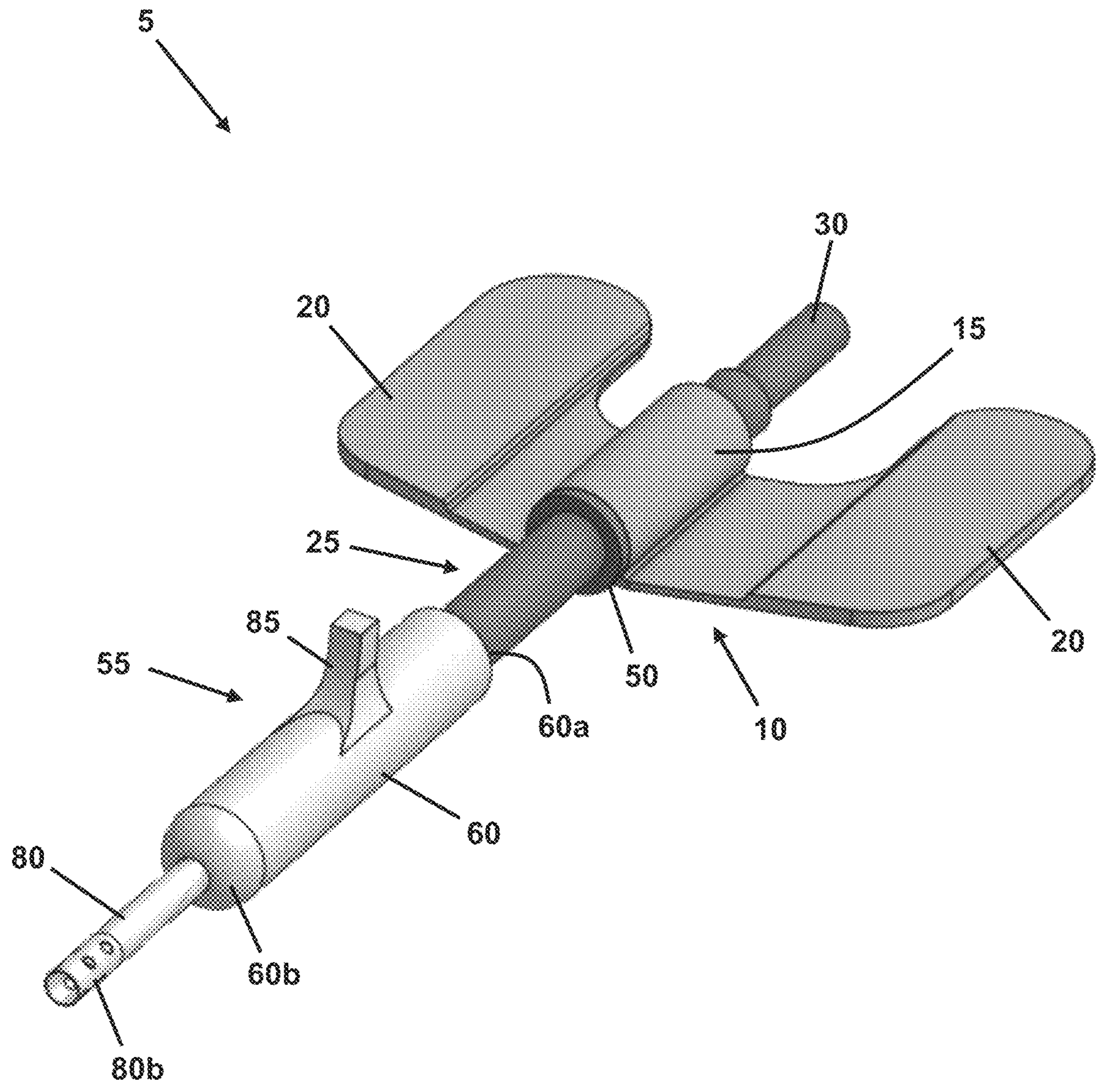
FIG. 2A is a top perspective view of the catheter device of FIG. 1A, with the catheter portion thereof in an extended position that covers the needle tip.
Figure 2B:
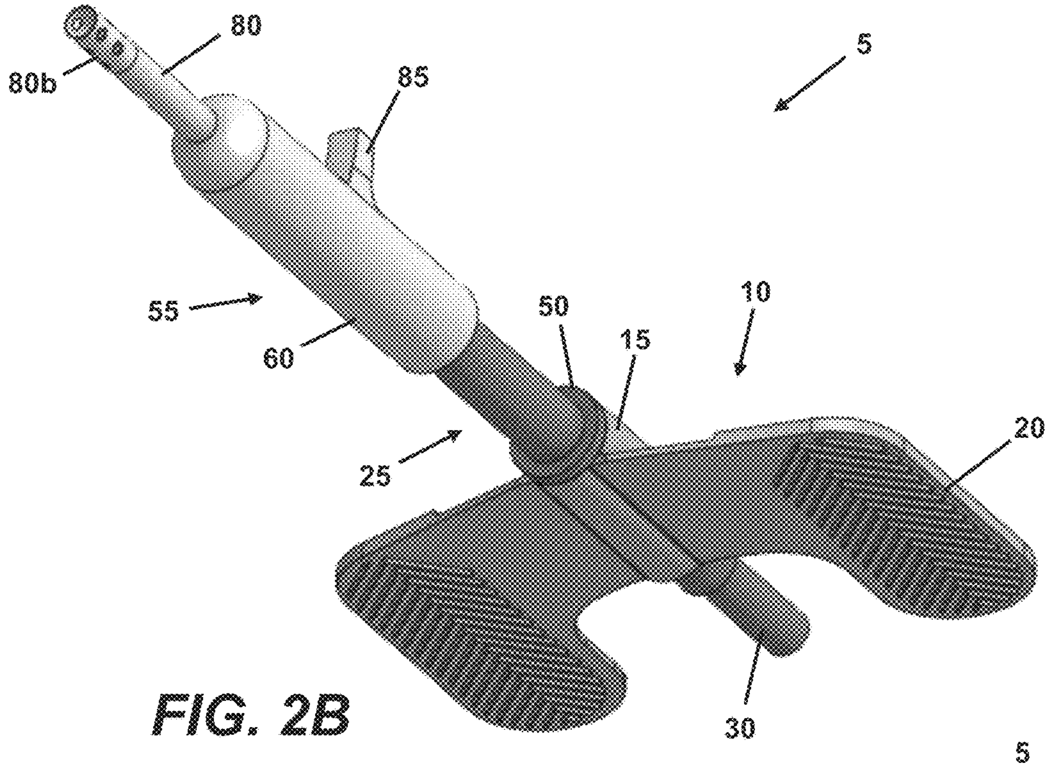
FIG. 2B is a bottom perspective view of the catheter device of FIG. 2A.
Figure 2C:
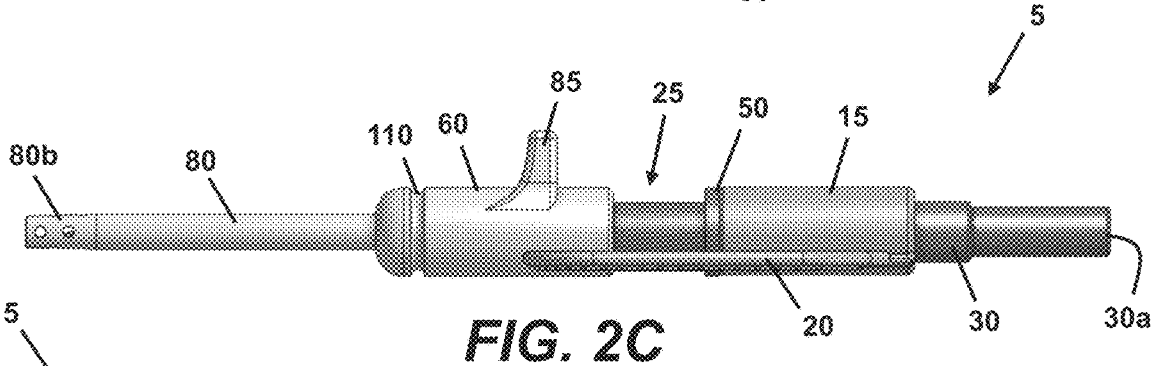
FIG. 2C is a side view of the catheter device of FIG. 2A.
Figure 2D:
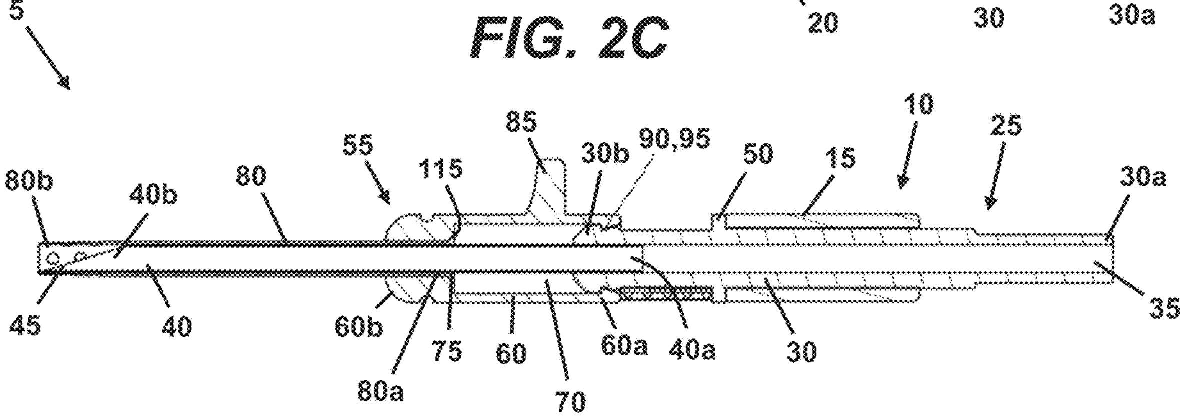
FIG. 2D is a cross-sectional view of the catheter device of FIG. 2C.

Referring to the sectional views of FIGS. 1D and 2D, it may be more specifically understood that abutting contact between the proximal end 60*a* of the catheter hub 60 and the distal side of the collar 50 of the needle hub 30 will act as a hard stop that can be used to set the proper retracted position of the catheter portion 55. It may also be observed that the exemplary catheter hub 60 of the exemplary catheter device 5 includes an inwardly-directed annular projection 90 at its proximal end 60*a*. The annular projection 90 may have a hook shape as shown, but other shapes are also possible. As explained further below, the annular projection 90 essentially acts as the lever element of the detent mechanism.

It may also be observed in FIGS. 1A and 2D that the needle hub 30 of the exemplary needle portion 25 is provided with an annular groove 95 near the distal end 30*b* thereof. The annular groove 95 essentially acts as the pawl element of the detent mechanism. As shown in FIG. 2D, when the catheter portion 55 is placed in the extended position, the annular projection 90 of the catheter hub 60 becomes releasably engaged with the annular groove 95 in the needle hub 30, thereby limiting the amount of possible linear movement and setting and retaining the extended position of the catheter portion 55, absent an overcoming displacement force provided by the user. Optionally, a second annular groove (not shown) may be similarly placed in the needle hub 30 in the area of the collar 50 to engage with the annular projection 90 of the catheter hub 60 and to releasably retain the catheter portion 55 in its retracted position absent an overcoming displacement force provided by the user.

Figure 3A:
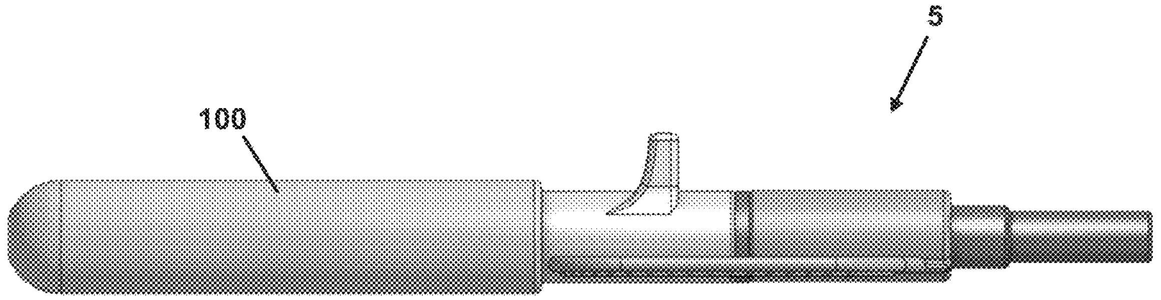
FIG. 3A depicts the catheter device of FIG. 10 with a protective cap.
Figure 3B:
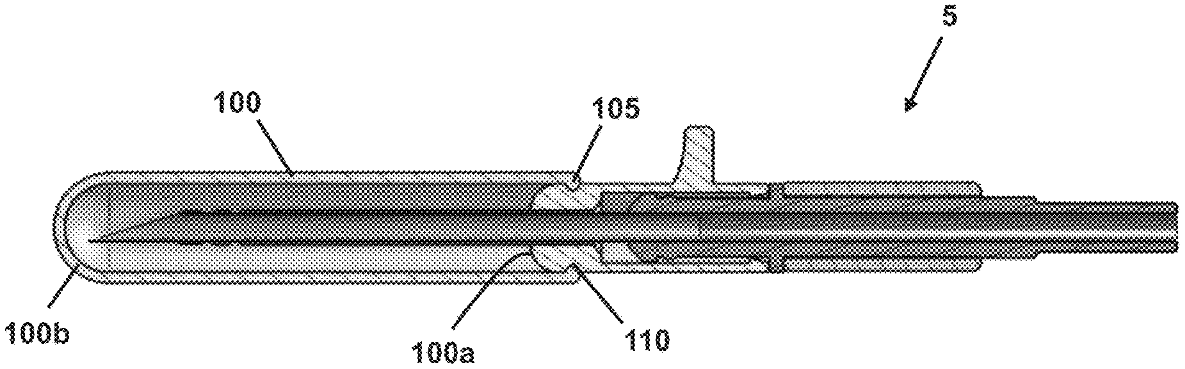
FIG. 3B depicts the catheter device of FIG. 3A with a section view of the protective cap.

To guard against inadvertent contact with the sharp tip 45 of the needle 40, a protective device may be associated with the needle. As illustrated in FIGS. 3A-3B, a cap 100 having an open proximal end 100*a* and a closed distal end 100*b* may be provided in this exemplary catheter device embodiment to enclose the needle 40 and catheter and to protect users from accidental needle sticks. When such a cap is provided, the cap may vary in shape and size. Such a cap may also be removably retained on the catheter device in different ways. In this example, the open end of the cap is provided with an inwardly-projecting retention ridge 105 that is located and configured to engage a corresponding annular cap retention groove 110 (see e.g., FIG. 10) provided in the catheter hub 60 near the distal end 60*b* thereof. Engagement of the retention ridge 105 with the cap retention groove 110 removably secures the cap 100 to the catheter hub 60.

Other cap retention techniques may be employed with other catheter device embodiments. Other exemplary catheter device embodiments may or may not include a cap.

Other exemplary catheter device embodiments also may utilize catheter portion position retaining mechanisms that differ from the particular detent mechanism shown in FIGS. 1D and 2D and described above. One exemplary embodiment of such an alternative position retention mechanism is depicted in FIGS. 4A-4D.

The exemplary arteriovenous catheter device 200 depicted in FIGS. 4A-4D again includes a body 205 and a catheter portion 225 that are supported on a needle portion 210. The design and interrelationship of each of the needle portion 205 and the catheter portion 225 is generally as described above, as is the basic concept of using the device 200 in a hemodialysis operation. Thus, the needle portion 210 again includes a needle hub 215 and a needle 220. Likewise, the catheter portion 225 again includes a catheter hub 230 and a catheter 235.

In the case of the exemplary arteriovenous catheter device 200 shown in FIGS. 4A-4D, the catheter portion retention mechanism employs a bolt element 240 having a shaft portion 245 that extends from the needle hub 215 through a detent groove 250 in the catheter hub 230 to limit movement and retain the position of the catheter portion 225 of the device relative to the needle portion 210 of the device. The shaft 245 of the bolt element 240 may include an enlarged end portion 255 to ensure the bolt element shaft 245 and the detent groove 250 in the catheter hub 230 remain engaged.

Figure 4A:
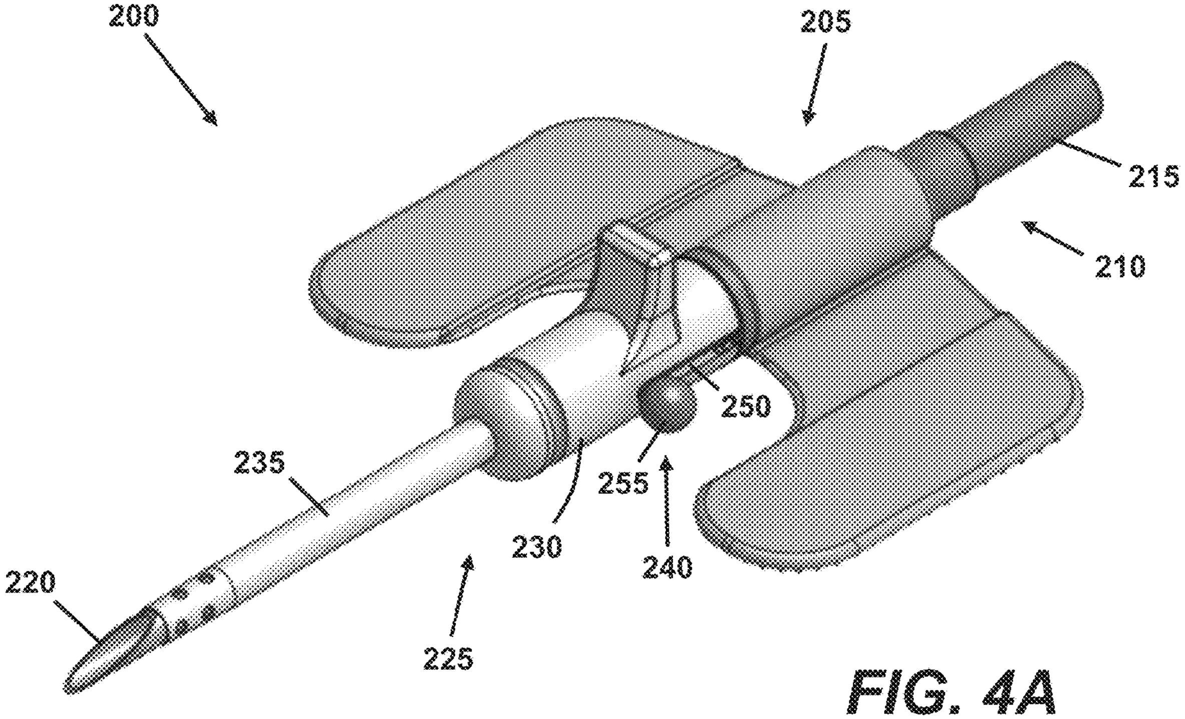
FIGS. 4A-4B are a top perspective view and a side view, respectively, of another exemplary embodiment of a catheter device according to the general inventive concept, with a catheter portion thereof in a retracted position that exposes a needle tip.
Figure 4B:
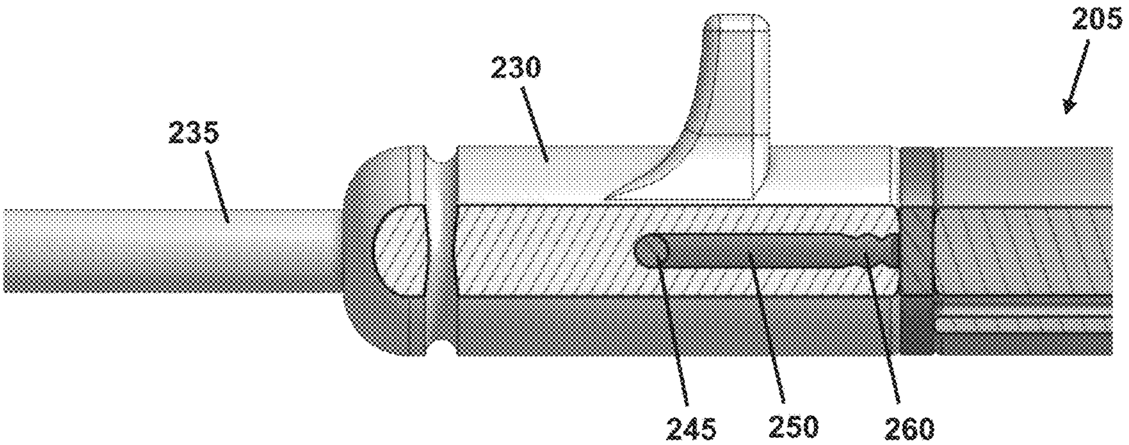
Figure 4C:
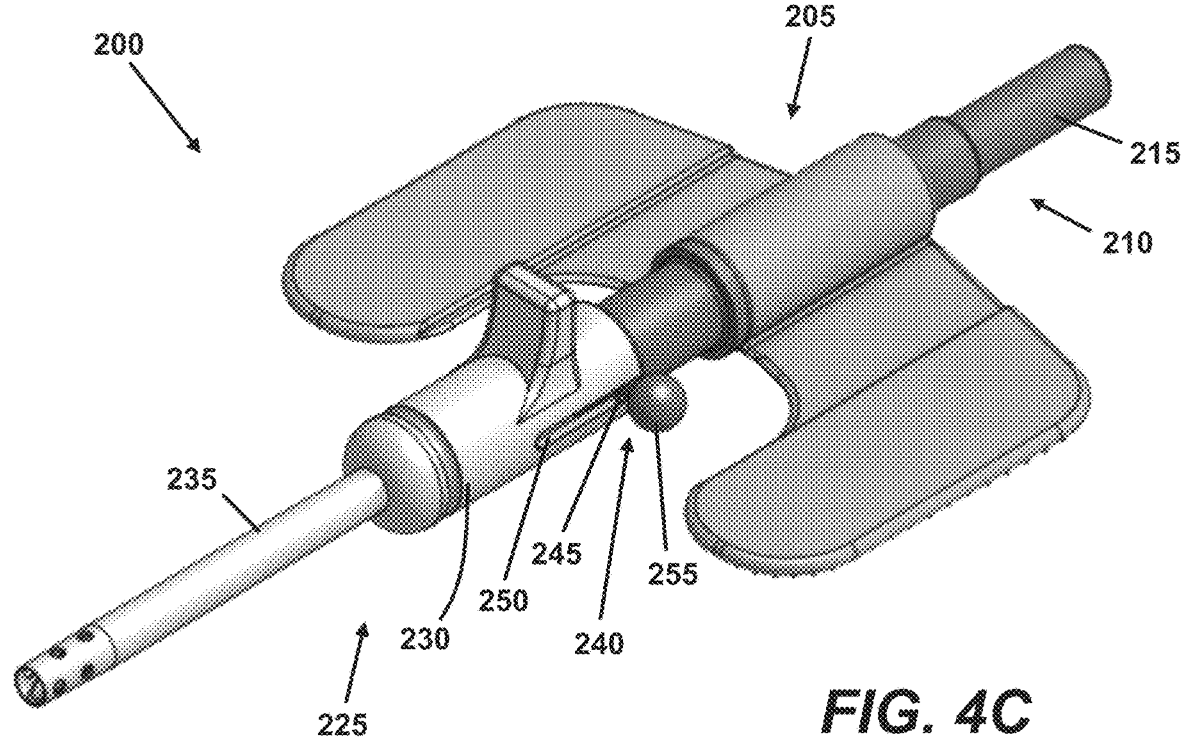
FIGS. 4C-4D are a top perspective view and a side view, respectively, showing the catheter device of FIGS. 4A-4B with the catheter portion thereof in an extended position that covers the needle tip.
Figure 4D:
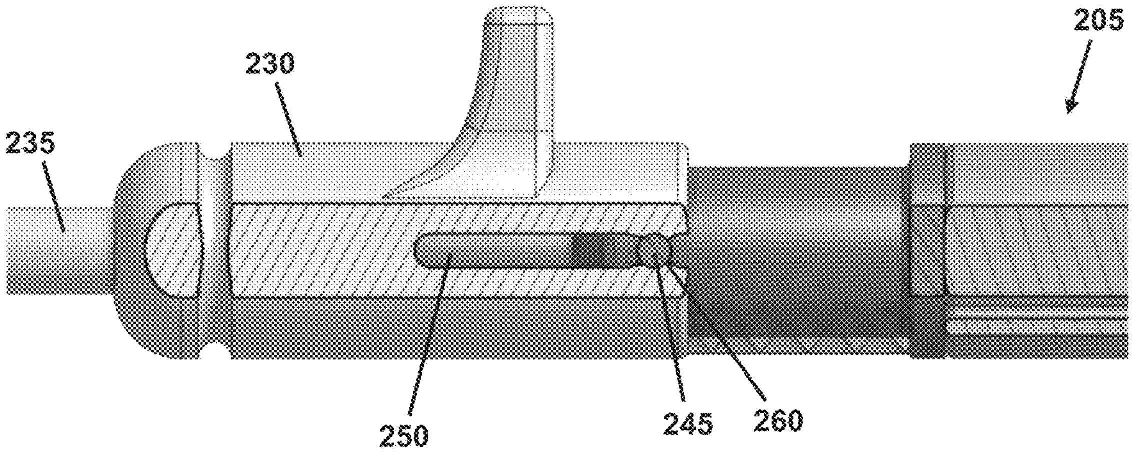

As shown most clearly in FIG. 4B, the detent groove 250 may be configured such that the shaft 245 of the bolt element 240 is in contact with the closed end of the detent groove 250 when the catheter portion 225 is in a retracted position. Referring also to FIG. 4D, it can be further observed that the detent groove 250 may include one or more detent notches 260 that are releasably engageable with the shaft 245 of the bolt element 240 when the catheter portion 225 is in an extended position. The interaction between the detent notches 260 and the shaft 245 of the bolt element 240 serves to retain the catheter portion 225 in the extended position unless an overcoming displacement force is provided by the user.

Another exemplary embodiment of an alternative catheter portion position retention mechanism is depicted in FIGS. 5A-5D. The exemplary arteriovenous catheter device 300 depicted in FIGS. 5A-5D again includes a body 305 and a catheter portion 325 that are supported on a needle portion 310. The design and interrelationship of each of the needle portion 305 and the catheter portion 325 is generally as described above, as is the basic concept of using the device 300 in a hemodialysis operation. Thus, the needle portion 310 again includes a needle hub 315 and a needle 320. Likewise, the catheter portion 325 again includes a catheter hub 330 and a catheter 335.

In the case of the exemplary arteriovenous catheter device 300 shown in FIGS. 5A-5D, the catheter portion retention mechanism employs a tab 340 that extends from the catheter hub 325 into a detent groove 345 in the needle hub 315 to limit movement and retain the position of the catheter portion 325 of the device relative to the needle portion 310 of the device. The tab 340 may be provided, for example, in the form of a pin.

Figure 5A:
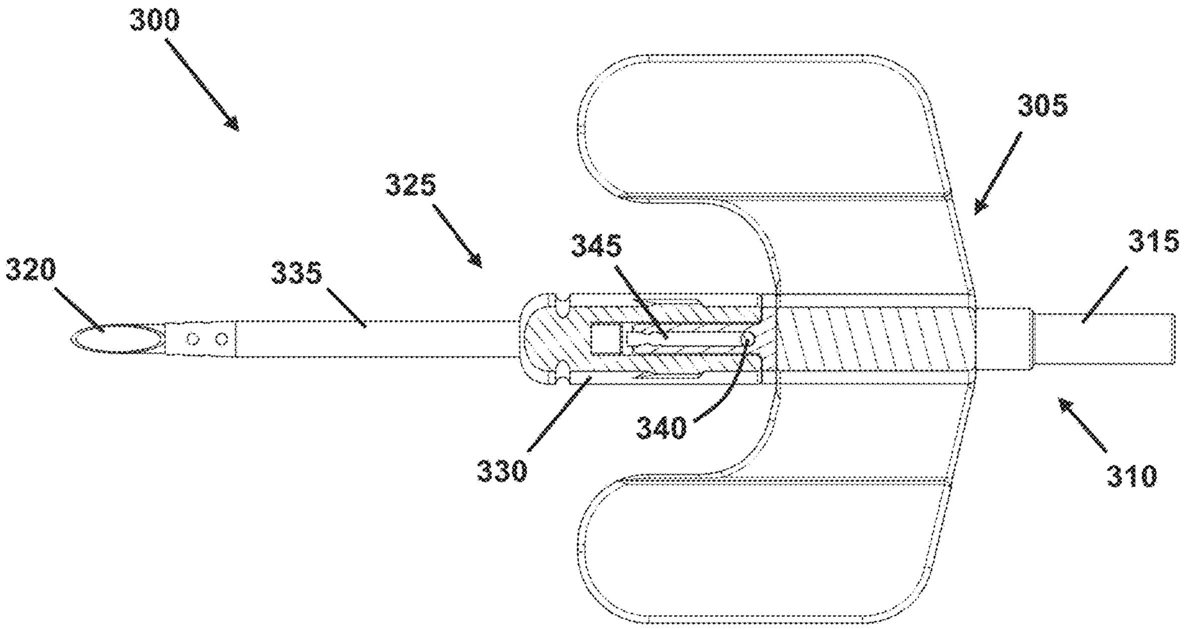
FIG. 5A is a top perspective view of another exemplary embodiment of a catheter device according to the general inventive concept, with a catheter portion thereof in a retracted position that exposes a needle tip.
Figure 5B:
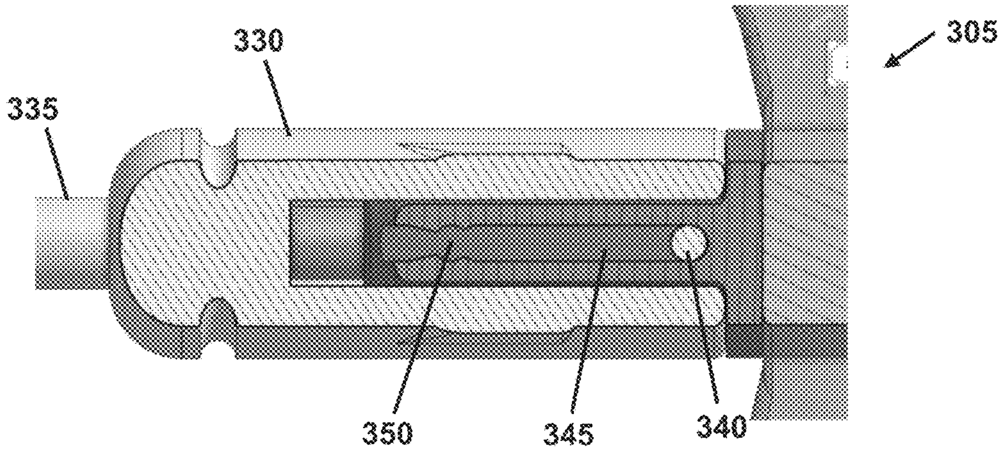
FIG. 5B is an enlarged top plan and partial section view of a portion of the catheter device of FIG. 5A.
Figure 5C:
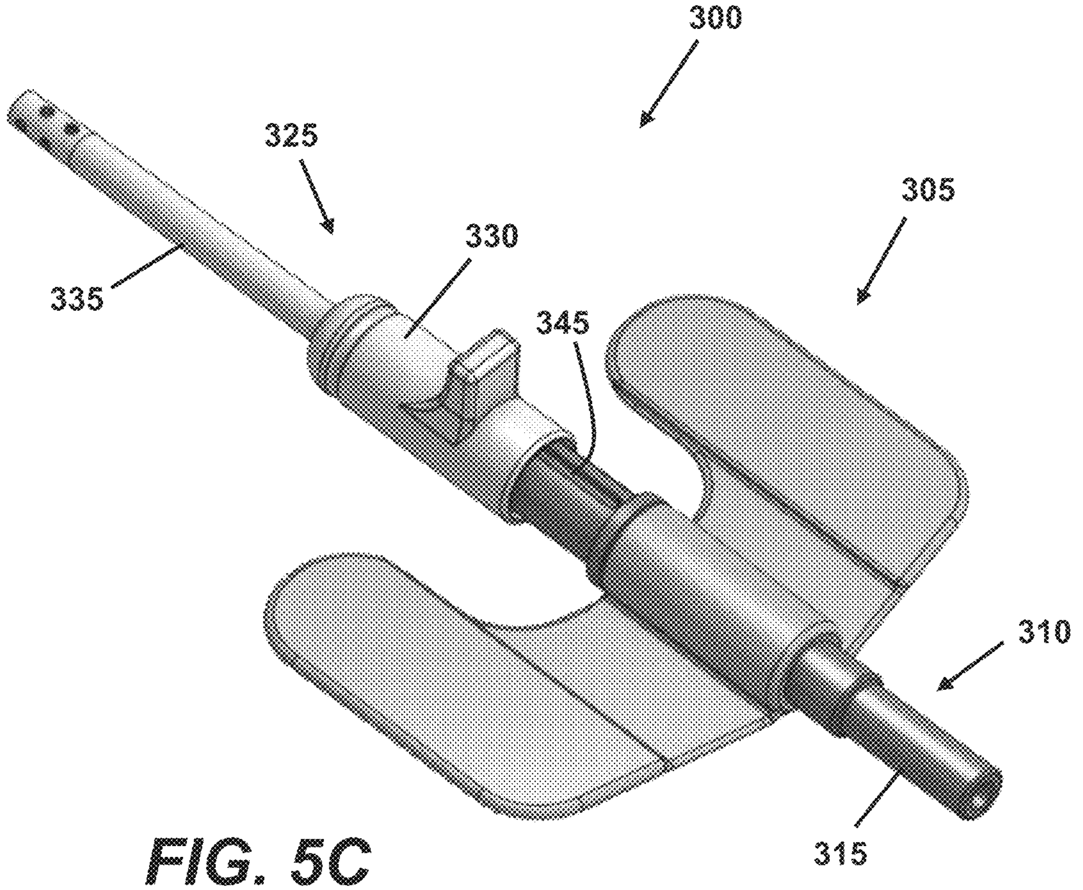
FIG. 5C shows the catheter device of FIG. 5A with the catheter portion in an extended position that covers the needle tip.
Figure 5D:
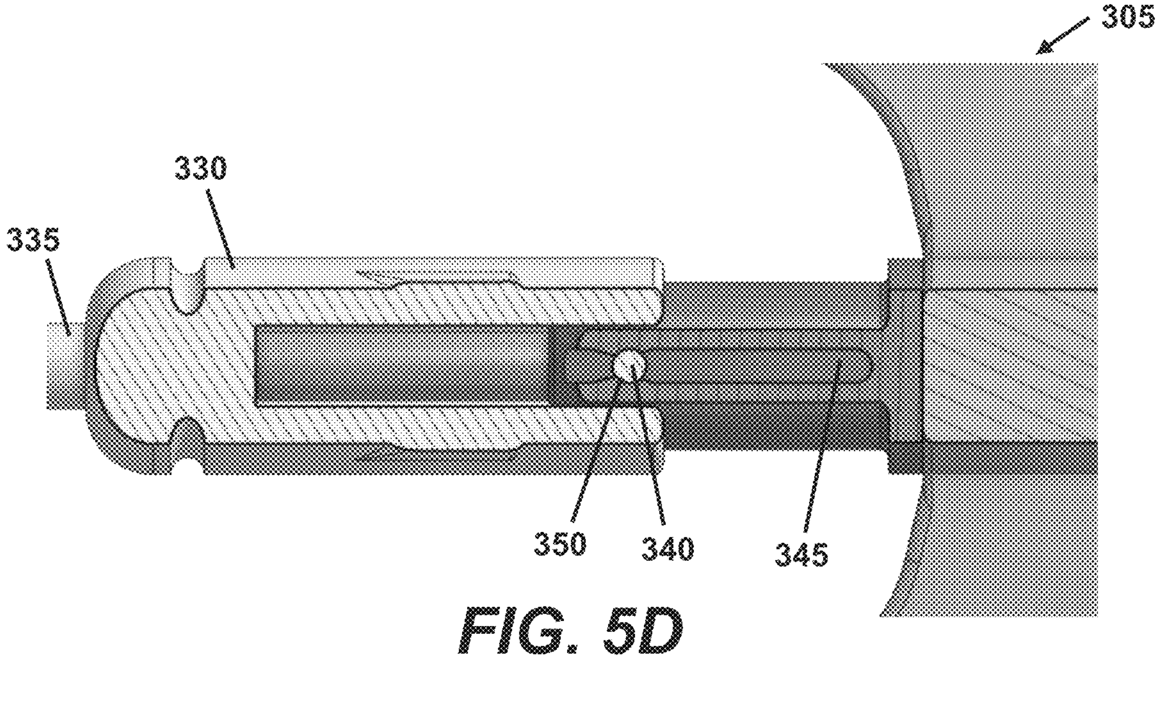
FIG. 5D is an enlarged top plan and partial section view of a portion of the catheter device of FIG. 5C.

As shown most clearly in FIG. 5B, the detent groove 345 may be configured such that the tab 340 is in contact with the closed end of the detent groove 345 when the catheter portion 325 is in a retracted position. Referring to FIG. 5D, it can also be observed that the detent groove 345 may include one or more detent notches 350 that are releasably engageable with the tab 340 when the catheter portion 325 is in an extended position. The interaction between the detent notches 350 and the tab 340 serves to retain the catheter portion 325 in the extended position unless an overcoming displacement force is provided by the user.

Figure 6A:
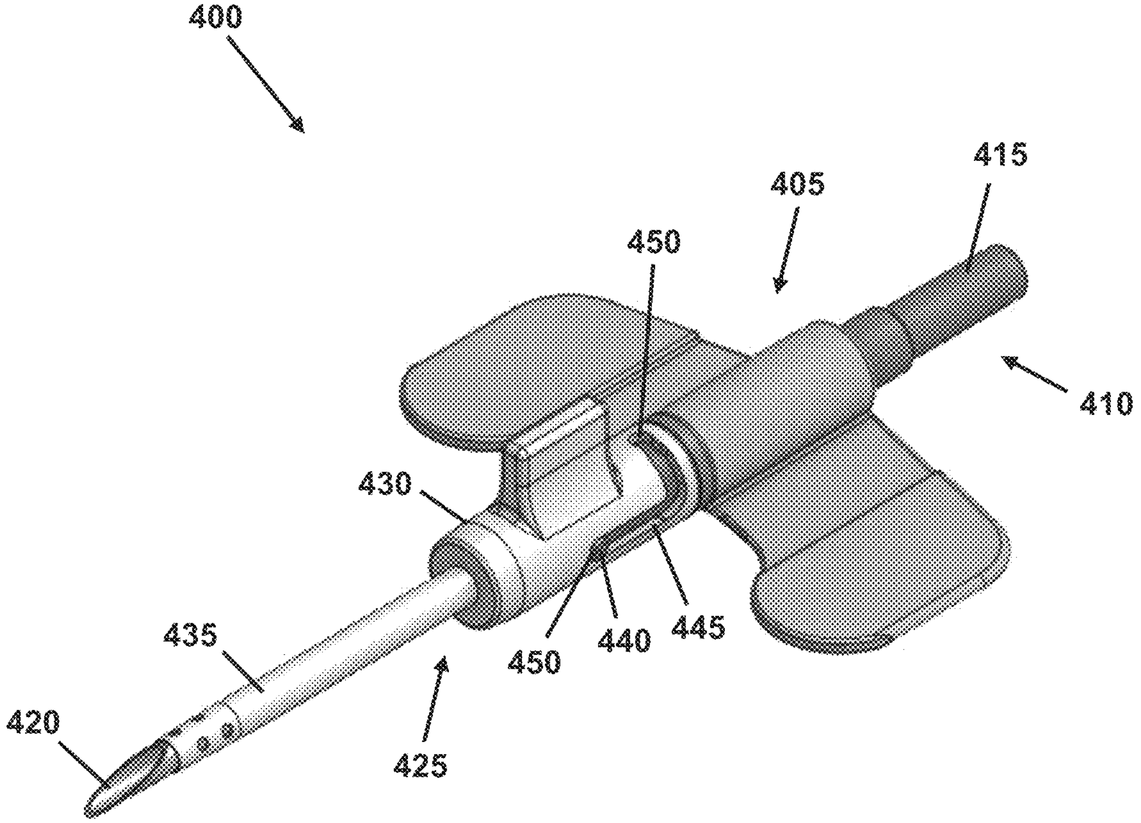
FIG. 6A is a top perspective view of another exemplary embodiment of a catheter device according to the general inventive concept, with a catheter portion thereof in a retracted position that exposes a needle tip.
Figure 6B:
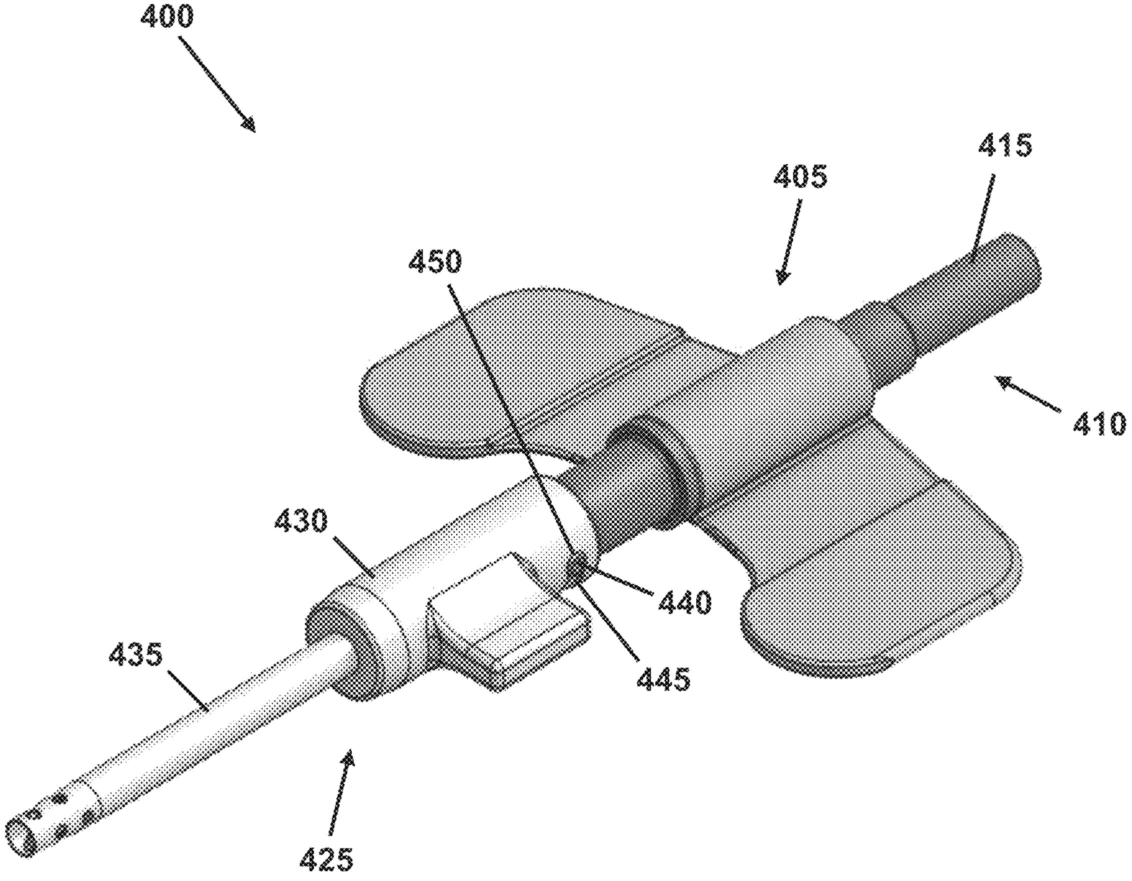
FIG. 6B shows the catheter device of FIG. 6A with the catheter portion in an extended position that covers the needle tip.

Another exemplary embodiment of an alternative catheter portion position retention mechanism is depicted in FIGS. 6A-6B. The exemplary arteriovenous catheter device 400 depicted in FIGS. 6A-6B again includes a body 405 and a catheter portion 425 that are supported on a needle portion 410. The design and interrelationship of each of the needle portion 410 and the catheter portion 425 is generally as described above, as is the basic concept of using the device 400 in a hemodialysis operation. Thus, the needle portion 410 again includes a needle hub 415 and a needle 420. Likewise, the catheter portion 425 again includes a catheter hub 430 and a catheter 435.

In the case of the exemplary arteriovenous catheter device 400 shown in FIGS. 6A-6B, the catheter portion retention mechanism employs a pin 440 that extends from the needle hub 415 through a curved cam slot 445 in the catheter hub 430 to limit movement and retain the position of the catheter portion 425 of the device relative to the needle portion 410 of the device. The cam slot 445 may be configured so as to wrap at least partially around the circumference of the catheter hub 430. As such, a linear displacement of the catheter hub 430 along the needle hub 415 will also produce a rotation of the catheter portion. During use of this exemplary arteriovenous catheter device 400, the cam slot 445 allows for parking of the catheter portion 425 in an extended position before final engagement, which permits minor adjustments to the catheter 435 and the needle 420 to obtain optimum blood flow.

Figure 7A:
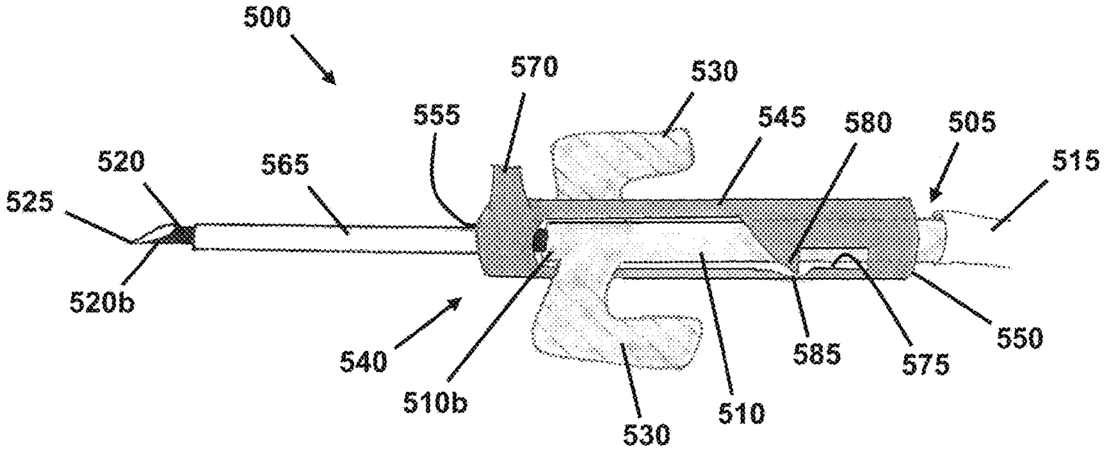
FIGS. 7A-7C are side views of another exemplary embodiment of a catheter device according to the general inventive concept, wherein a catheter portion of the device is respectively shown in a fully retracted, partially extended and fully extended position.
Figure 7B:
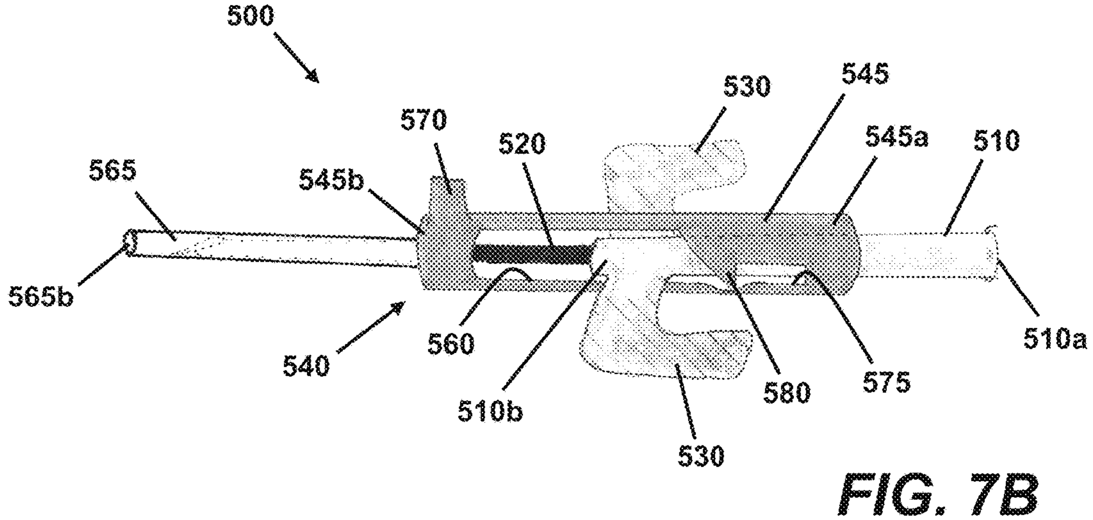
Figure 7C:
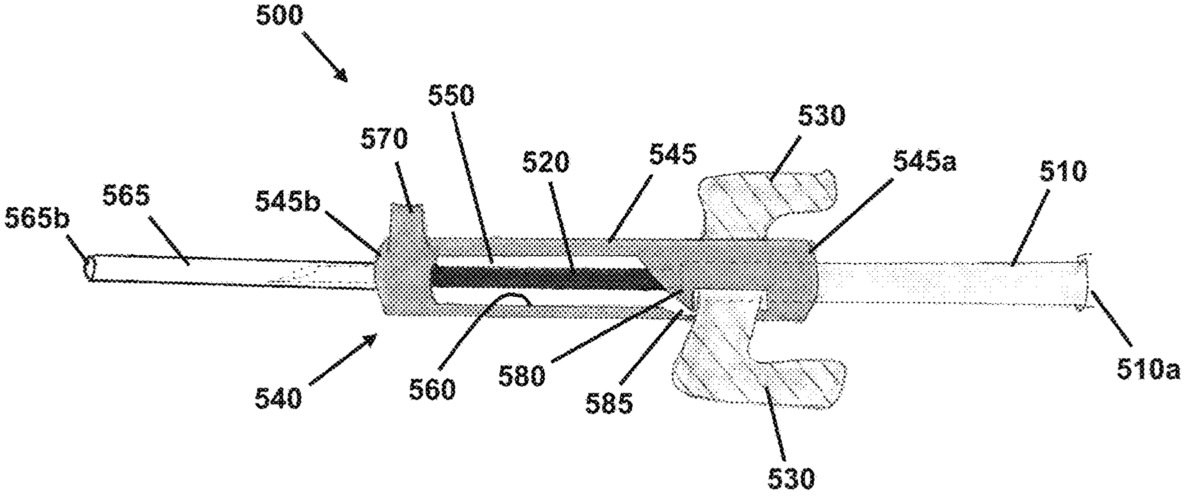

Another exemplary embodiment of a vascular access catheter device 500 is illustrated in FIGS. 7A-7C. As may be observed, the device 500 includes a needle portion 505 and a catheter portion 540. The needle portion 505 includes an elongate needle hub 510 having a proximal end 510*a* and a distal end 510*b*. A hollow interior of the needle hub provides a pathway for blood flow during a hemodialysis procedure or when the device is otherwise used to access peripheral vessels. Tubing 515 may be coupled to the proximal end 510*a* of the needle hub 510 for connecting the catheter device 500 to a hemodialysis machine or to another device, as would be understood by one of skill in the art.

A needle 520 of the needle portion 505 has a proximal end (not visible) thereof that may be inserted sufficiently far into the bore at the distal end 510*b* of the needle hub 510 to securely retain the needle therein. The proximal end of the needle 520 may be retained in the needle hub 510 by a press fit or a similar interaction between the components. Alternatively, or in conjunction with such other techniques, an adhesive or other affixation mechanism may be used to further secure the needle 520 in the needle hub 510. A distal, free end 520*b*, of the needle is provided with a sharp point 525 for the purpose of piercing the skin of a patient and subsequently accessing a fistula/graft or peripheral vessel. The specific needle gauge, needle construction, etc., may vary in keeping with accepted practices understood in the art.

The needle portion 505 in this exemplary embodiment further includes a pair of wing-like gripping elements 530 that extend substantially laterally outward from opposite sides of the needle hub 510. While the gripping elements 530 may be of various shapes, in this exemplary embodiment the gripping elements 530 of the body are shaped as shown to facilitate gripping and manipulation of the device 500 by a user and taping of the device to a limb of a patient after fistula/graft or peripheral vessel access.

As previously described, the exemplary catheter device 500 also includes a catheter portion 540 that is supported on the needle portion 505 and includes a catheter hub 545 with proximal and distal ends 545*a*, 545*b*. The size and shape of the catheter hub 545 is selected so that the catheter hub will cooperate with the needle hub 510. More specifically, the catheter hub 545 is of substantially cylindrical shape, and includes a first central (needle hub-receiving) bore 550 at the proximal end 545*a* that renders the needle hub substantially hollow and is dimensioned to permit the catheter hub to slide over the needle hub 510. This arrangement allows the catheter portion 540 of the catheter device 500 to be supported on the needle portion 505 and for the catheter hub 540 and the needle hub 510 to slide linearly relative to one another as illustrated in FIGS. 7A-7C. A smaller diameter second central bore 555 (see also FIG. 8B) extends inward from the distal end 545*b* of the catheter hub 545 and opens into the needle hub receiving bore 550 to allow passage of the needle 520 through the distal end of the catheter hub 545.

The catheter hub 545 of this exemplary catheter device 500 further includes a pair of diametrically opposed gripping element relief slots 560, through which the gripping elements 530 of the needle portion 505 may protrude when the catheter portion 540 is properly installed over the needle portion 505. If an exemplary catheter device embodiment utilizes only a single gripping element 530, the catheter hub 545 may, but is not required to, include only one corresponding gripping element relief slot 560.

The catheter portion 540 further includes a hollow catheter 565 that extends longitudinally outward from the distal end 545*b* of the catheter hub 545 and includes open proximal and distal ends. In some embodiments, the proximal end (not visible) of the catheter 565 may be inserted sufficiently far into the second central bore 555 in the catheter hub 545 to securely retain the catheter therein. In such an embodiment, the proximal end of the catheter 565 may be retained in the catheter hub 545 by any of the needle retention techniques mentioned above or by any other acceptable technique known to one of skill in the art. In other embodiments, the catheter 565 may be an integrally molded part of the catheter hub 545. A distal, free open end 565*b*, of the catheter 565 may be tapered and/or may include any other features that may facilitate entry of the free end of the catheter into the fistula/graft or peripheral vessel of the patient subsequent to initial access by the needle 520 and/or may facilitate blood flow during a hemodialysis or other vascular access procedure.

The inside diameter of the catheter 565 is preferably similar in dimension to the outside diameter of the needle 520 so as to produce a close tolerance sliding fit between the catheter 565 and the needle 520 when the catheter hub 545 is installed over the needle hub 510. Nonetheless, a seal 590 (see FIG. 8B) may be placed at or near the entry point of the second bore 555 into the first bore 550 to prevent possible blood leakage between the needle 520 and the catheter 565 during use of the catheter device 500. As with the needle 520, the specific construction of the catheter 565 may otherwise vary in keeping with accepted practices understood in the art. For example, the catheter 565 may be constructed from a fluoroplastic material.

From the foregoing description and corresponding FIGS. 7A-7C, it should be understood that when the catheter portion 540 is properly assembled to the needle portion 505, as explained above, a portion of the needle hub 510 is substantially concentrically located within the catheter hub 545, a portion of the needle 520 is substantially concentrically located within the catheter 565, and the catheter hub 545 and attached catheter 565 are together linearly slidable relative to the needle hub 510 and the attached needle 520. As shown in the drawing figures, a grip 570 or similar feature may be provided on the catheter hub 545 to facilitate sliding of the catheter portion 540 by a user of the device 500.

FIG. 7A shows a position where the needle portion 505 is fully extended relative to the catheter portion 540 (or the catheter portion is fully retracted relative to the needle portion), which results in the needle tip 525 and perhaps some additional length of the needle 520 protruding from the open distal end 565*b* of the catheter. This is the proper positioning of the needle portion 505 and the catheter portion 540 for initial piercing of the patient's skin and accessing of the underlying fistula/graft or peripheral vessel using the needle 520 of the catheter device 500.

After the tip of the needle 520 has been inserted into the patient's fistula/graft or peripheral vessel, the catheter portion 540 may be moved toward an extended position (see FIGS. 7A-7C) by sliding the catheter portion linearly and in a proximal-to-distal direction along the needle hub 510 such that the sharp tip 525 of the needle 520 becomes covered by the distal end 565*b* of the catheter 565 and a portion of both the needle and the catheter temporarily reside in the fistula/graft or peripheral vessel. The grip 570 on the catheter hub 545 may be used to facilitate linear movement of the catheter portion 540.

Once blood flash is seen in the catheter 565, the needle portion 505 may be slid slightly in a proximal or distal direction to move the needle 520 relative to the catheter 565 and to resultantly achieve optimum blood flow and position. The needle portion 505 may then be "parked" in this position, but the positional relationship of the catheter 565 and needle 520 may also be further adjusted if needed to maintain an optimized blood flow. Once the final desired position of the catheter 565 and optimized blood flow is achieved, the needle portion 505 is retracted (such as by using the gripping elements 530) relative to the catheter portion 540 until travel of the needle portion is halted by a hard stop and the needle portion reaches an irreversible position (as explained below). With the catheter 565 properly located in the fistula/graft or peripheral vessel of the patient and the needle portion 505 placed in the irreversible retracted position, the catheter device 500 may be secured to the limb of the patient using tape or another technique known in the art.

As should be readily obvious to one of skill in the art, placing the catheter 565 of the exemplary catheter device 500 into the fistula/graft or peripheral vessel and over the needle tip 525 as described above serves to prevent the needle tip from damaging the fistula/graft or peripheral vessel and also, therefore, prevents infiltration and related hematoma problems. And unlike known devices, the needle 520 of the exemplary catheter device 500 remains partially within the catheter 565 during a hemodialysis or other vascular procedure, thereby substantially eliminating any chance that the catheter may collapse, kink, etc., and interfere with blood flow or cause damage on its own.

As described above, the catheter portion 540 has a retracted position where the catheter 565 is kept from interfering with use of the needle 520 to initially access the fistula/graft or peripheral vessel of a patient. Likewise, the needle portion 505 has an extended position that corresponds to the retracted position of the catheter portion 540 and a retracted position where the needle 520 is drawn into the catheter 565 and out of the fistula/graft or peripheral vessel once the catheter is inserted therein and blood flow has been optimized. Consequently, in addition to securing the overall catheter device 500 to the patient, it is also preferable to provide mechanisms by which it can be ensured that the position of the catheter portion 540 relative to the position of the needle portion 505 will be maintained after the needle 520 has been fully retracted.

As may be understood from FIG. 7A, contact between the distal end 510*b* of the needle hub 510 and the interior wall of the distal end of the catheter hub 545, and/or contact between a leading edge of the gripping elements 530 and a distal terminus of the gripping element relief slots 560 may act as a hard stop and set the fully extended position of the needle portion 505 and the fully retracted position of the catheter portion 540.

Referring to FIGS. 7B-7C, it may be observed that in the case of the exemplary catheter device 500, a needle portion retraction hard stop and needle portion retracted position retention functionality are both provided via interaction of certain elements of the catheter hub 545 and the needle hub 510. More specifically, the proximal end of at least one of the gripping element relief slots 560 in the catheter hub 545 leads into a needle portion retention mechanism having a retention slot 575 that extends further toward the proximal end 545*a* of the catheter hub.

The needle portion retention mechanism also includes a retention tab 580—which may be an integral portion of the catheter hub 545. The retention tab 580 protrudes into the retention slot 575 near a distal end thereof. The retention tab 580 may be shaped to facilitate passage of the corresponding needle portion gripping element 530—which also comprises an element of the needle portion retention mechanism—when the needle portion is moved in a distal-to-proximal direction relative to the catheter portion 540 toward its fully retracted position, but to prevent passage of the gripping element upon a subsequent attempt to thereafter move the needle portion in a proximal-to-distal direction back toward its extended position. For example, and as shown, the retention tab 580 may have a distal (leading) edge that slopes toward the proximal end 545*a* of the catheter hub 545, but a proximal (trailing) edge that is substantially parallel to the proximal end of the catheter hub (i.e., substantially transverse to the central axis of the device 500). Other retention tab trailing edge shapes may also be possible, as long as the trailing edge of the retention tab 580 is operative to engage the leading edge of the gripping element 530 and to prohibit an extending motion of the needle portion 505 once the needle portion has reached its fully retracted position.

The retention tab 580 may be aligned with a recess 585 or similar contour in the retention slot 575 to facilitate passage of the gripping element 530 past the retention tab 580 during an extending movement of the catheter portion 540. Passage of the gripping element 530 past the retention tab 580 during an extending movement of the catheter portion 540 may be instead or further facilitated by some controlled degree of flexibility of the retention tab 580 and/or the gripping element 530. For example, it will be common for a user to bend the gripping elements 530 when displacing the needle portion 505 during insertion or retraction of the needle 520 and to return the gripping elements to a substantially flat position before taping the catheter device 500 to a limb of a patient. Such a bending of the gripping elements 530 may also assist in passage of the gripping elements past the retention tab 580 of the retention mechanism during retraction of the needle portion 505.

As may be best observed in FIG. 7C, the position of the retention tab 580 and the size and shape of the portion of the retention slot 575 that resides proximally of the retention tab is such to accommodate a corresponding portion of the gripping element 530. More particularly, said portion of the retention slot 575 is preferably of like shape and only slightly larger than the corresponding portion of the gripping element 530 so as to trap the corresponding portion of the gripping element 530 between the trailing edge of the retention tab 580 and a proximal terminus of the retention slot 575, and to minimize or prohibit any further linear movement of the catheter portion 540 relative to the needle portion 505. Abutting contact between the proximal terminus of the retention slot 575 and a proximal edge of the gripping element 530 also functions as a hard stop for the fully retracted position of the needle portion 505. Likewise, the size and shape of the portion of the retention slot 575 that resides proximally of the retention tab also substantially prevents any rotation of the catheter portion 540 relative to the needle portion 505 when the needle portion is in a fully retracted position.

Figure 8A:
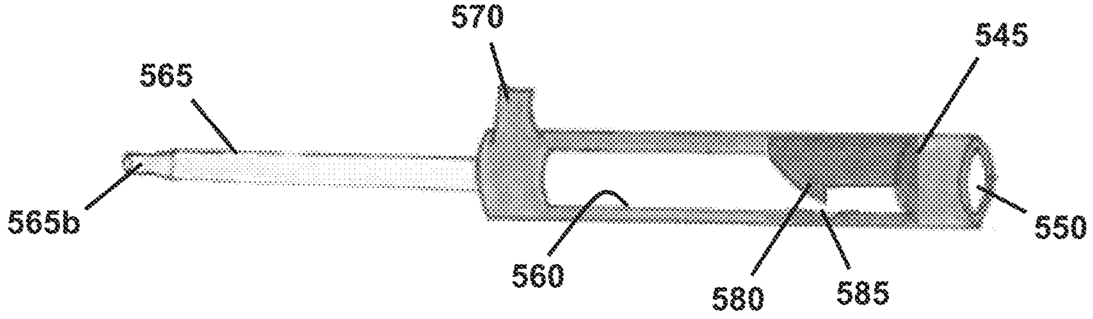
FIGS. 8A-8B depict a perspective view and a cross-sectional side view, respectively, of an exemplary catheter portion of an exemplary embodiment of a catheter device according to the general inventive concept.
Figure 8B:
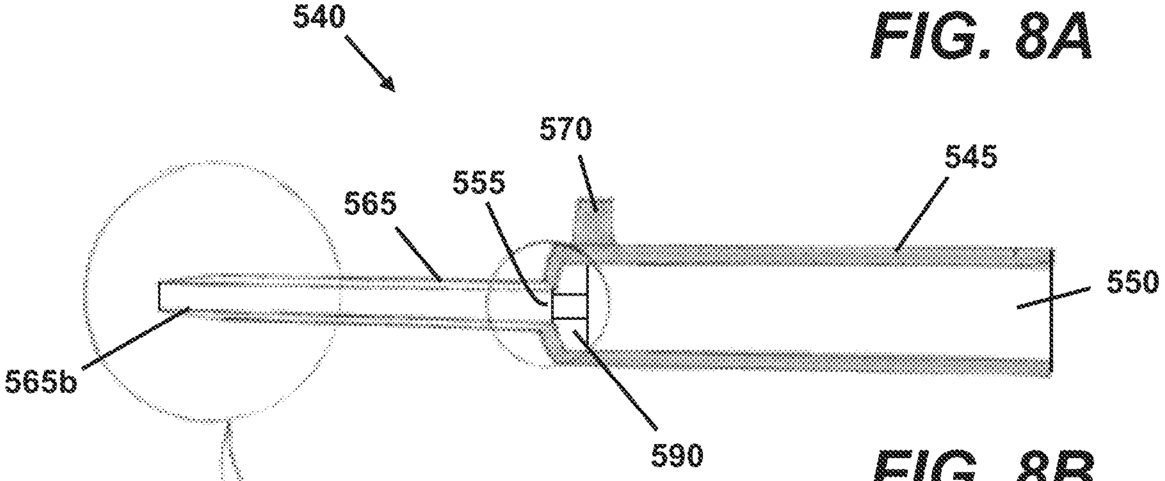

For further reference and clarity, a perspective view and a cross-sectional side view of the exemplary catheter portion 540 of the exemplary catheter device 500 of FIGS. 7A-7C is shown in FIGS. 8A and 8B, respectively. As previously stated, the dimensions of a given catheter device according to the inventive concept may vary as needed. However, in the exemplary embodiment of the device 500 of FIGS. 7A-7C, the length of the catheter hub 540 may be about 38 mm; the outside diameter of the catheter hub may be about 5.6 mm; the inside diameter (bore 550) of the catheter hub may be about 4 mm (for a wall thickness of about 0.8 mm); the length of the gripping element relief slot(s) 560 in the catheter hub may be about 17 mm; the length of the catheter 565 may be about 17 mm; the inside diameter of the catheter may be about 1.9 mm; and the catheter may have a wall thickness of about 0.25 mm.

Figure 8C:
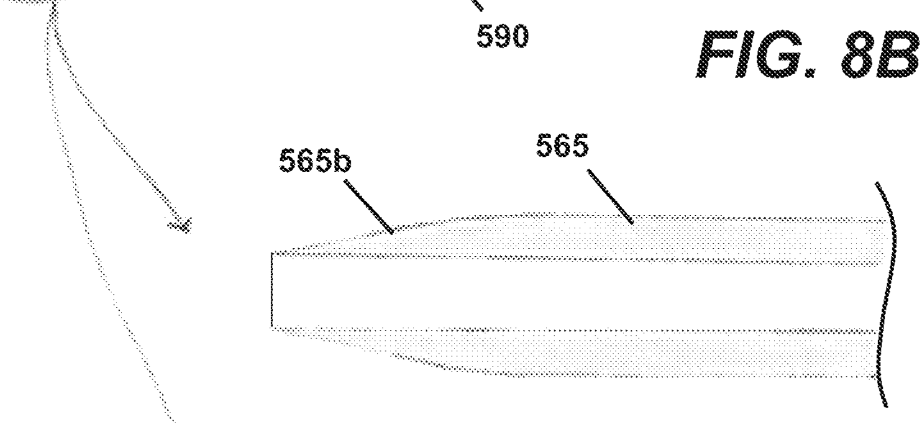
FIGS. 8C-8D depict various possible features of an insertion end of an exemplary catheter of an exemplary catheter portion such as that shown in FIGS. 8A-8B.
Figure 8D:
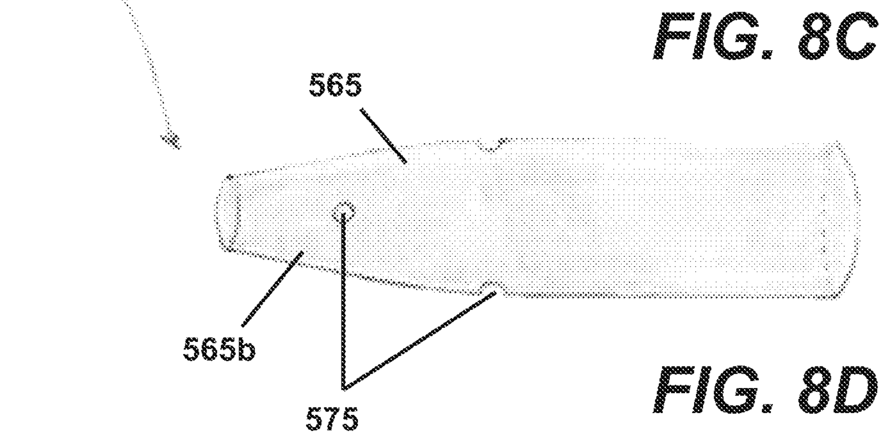

As further illustrated in FIGS. 8C-8D, the catheter 565 may have a tapered distal end 565*b* to facilitate insertion into the hole in a patient's skin and fistula/graft or peripheral vessel created by the leading end of the needle 520. A plurality of orifices 575 may also be distributed about the distal end 565*b* of the catheter 565 to optimize blood flow into the catheter. For example, four diametrically opposed smooth orifices 575 may be present and each orifice may have a diameter of about 0.7 mm.

The material(s) used to produce the exemplary device 500 may also vary. For example, parts of the device 500 other than the needle 520 may be comprised of one or more thermoplastic polymers. In this regard, it has been found that manufacturing the catheter hub 545 from a polycarbonate, polyethylene or polypropylene material provides good results, as does manufacturing the catheter from polyethylene, polypropylene or flouroethylenepropylene (FEP). The needle 520 may be comprised of an acceptable metallic material or of any other material that is currently known to be acceptable or hereafter becomes acceptable in the art.

Another exemplary embodiment of a vascular access catheter device 600 is illustrated in FIGS. 9A-14. As may be best observed in FIGS. 9A-9B and 10A-10C, the device 600 includes a needle portion 605 having an elongate, hollow, needle hub 610 from which extends a needle 615, and a catheter portion 700 having a hollow body 705 with a projecting and hollow catheter hub 710. A catheter 715 extends forward from the catheter hub 710.

As may be better observed in FIGS. 11A-13C, the needle portion 605 and the catheter portion 700 are assembled to one another such that the needle hub 610 of the needle portion 605 is located within the body 705 of the catheter portion, and the needle 615 of the needle portion extends through the catheter hub 705 and into/through the catheter 715 of the catheter portion. The needle portion 605 and the catheter portion 700 are designed and assembled so as to be slidable relative to one another, which allows the needle 615 to be extended and retracted relative to the catheter 715 during use of the device 600, as is described in more detail below. The combination of the hollow catheter 715, the hollow needle 615 and the cooperating hollow interior of the needle hub 610 provides a pathway for blood flow during a hemodialysis procedure or when the device 600 is otherwise used to access peripheral vessels.

Figure 9A:
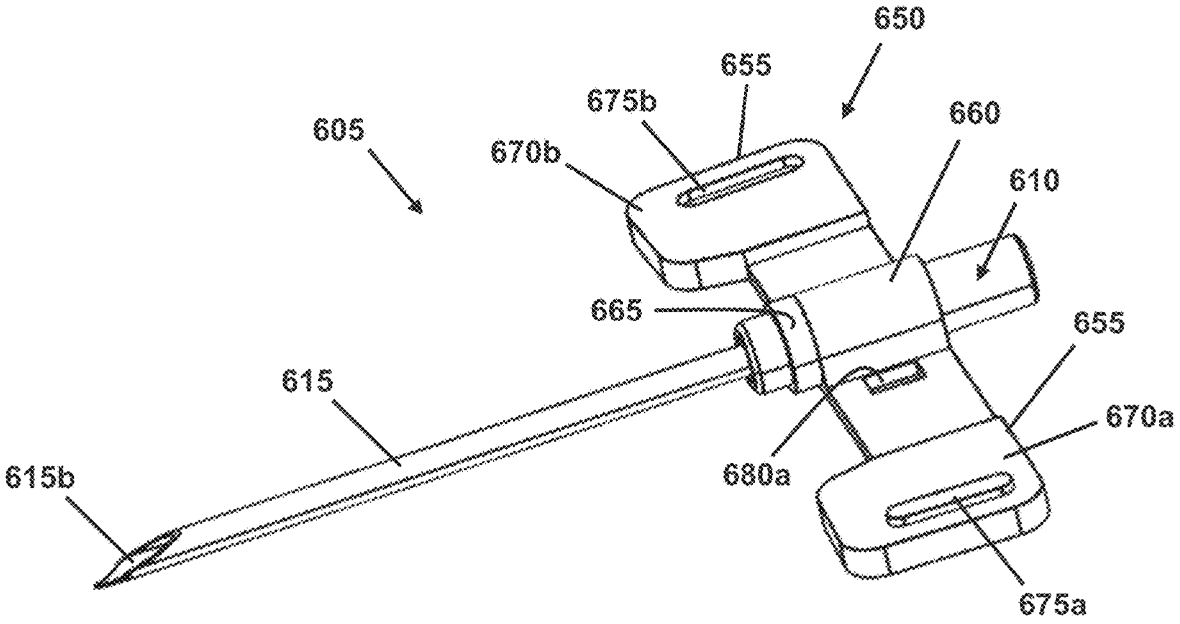
FIGS. 9A-9B are various perspective views of a needle portion of another exemplary embodiment of a vascular access catheter device according to the general inventive concept.
Figure 9B:
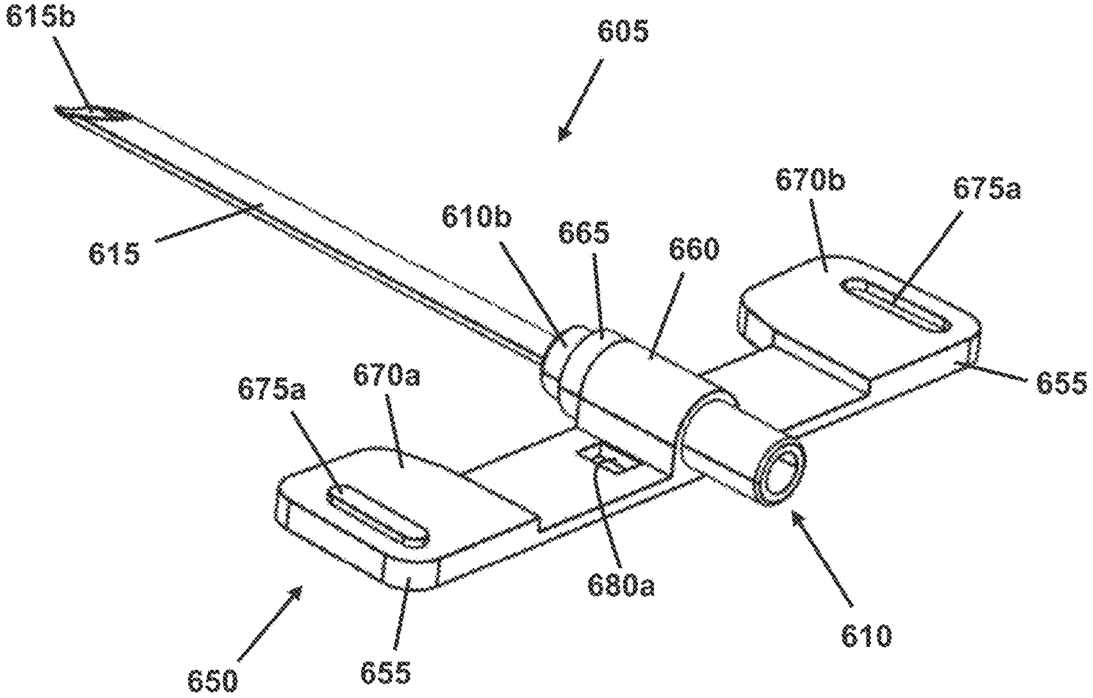
Figure 11A:
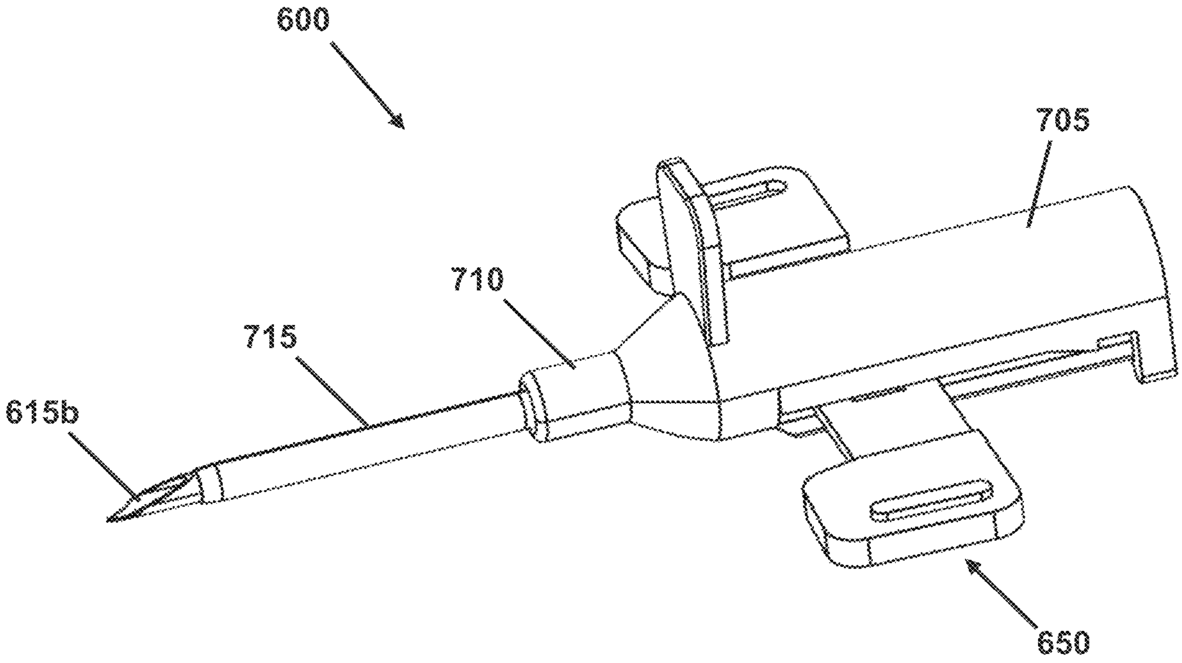
FIG. 11A is a perspective view of an exemplary embodiment of a vascular access catheter device comprising the needle portion of FIGS. 9A-9B assembled with the catheter portion of FIGS. 10A-10C, and wherein the catheter portion of the device is respectively shown in a retracted position that exposes a needle tip of the needle portion.
Figure 11B:
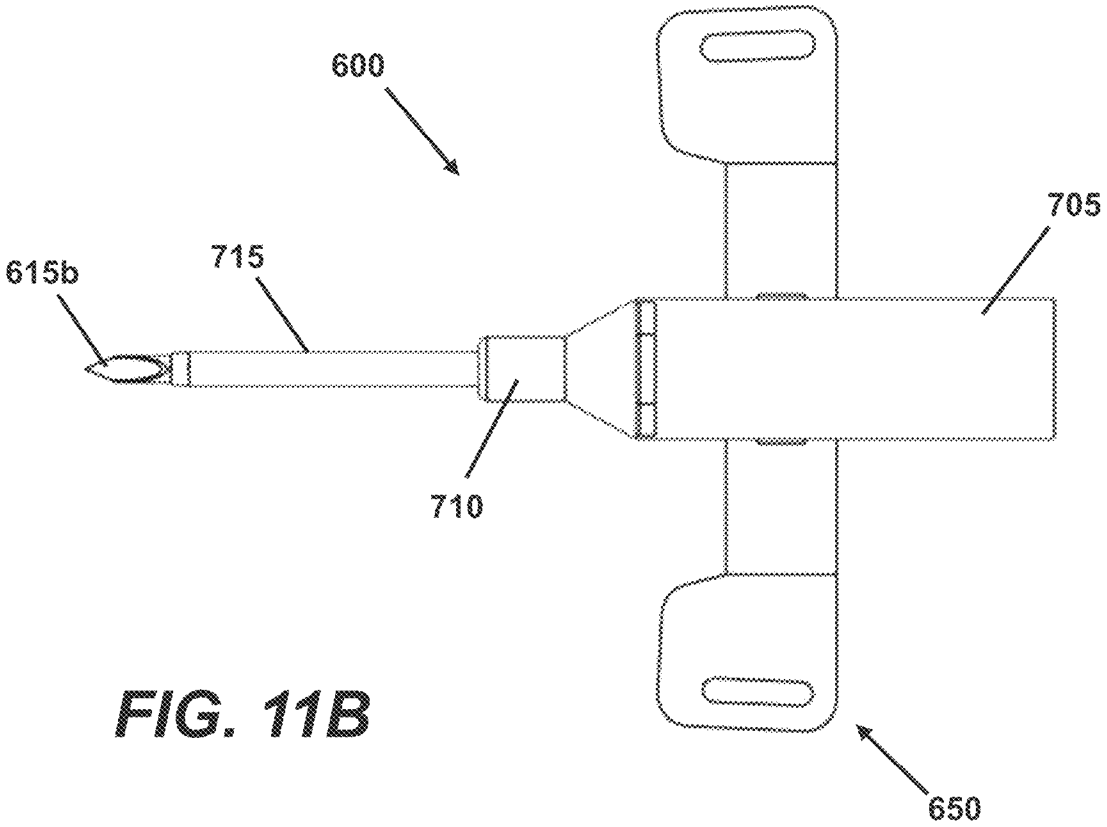
FIG. 11B is a top view of the catheter device shown in FIG. 11A.
Figure 11C:
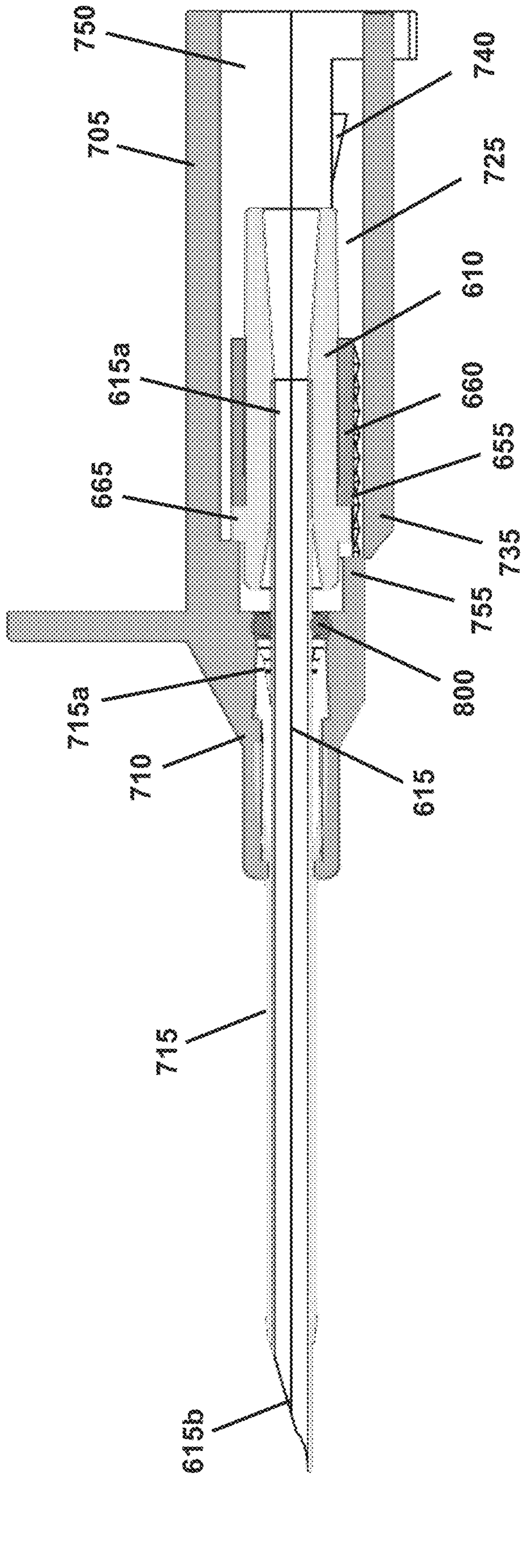
FIG. 11C is an enlarged cross-sectional side view of the catheter device shown in FIG. 11A.
Figure 12A:
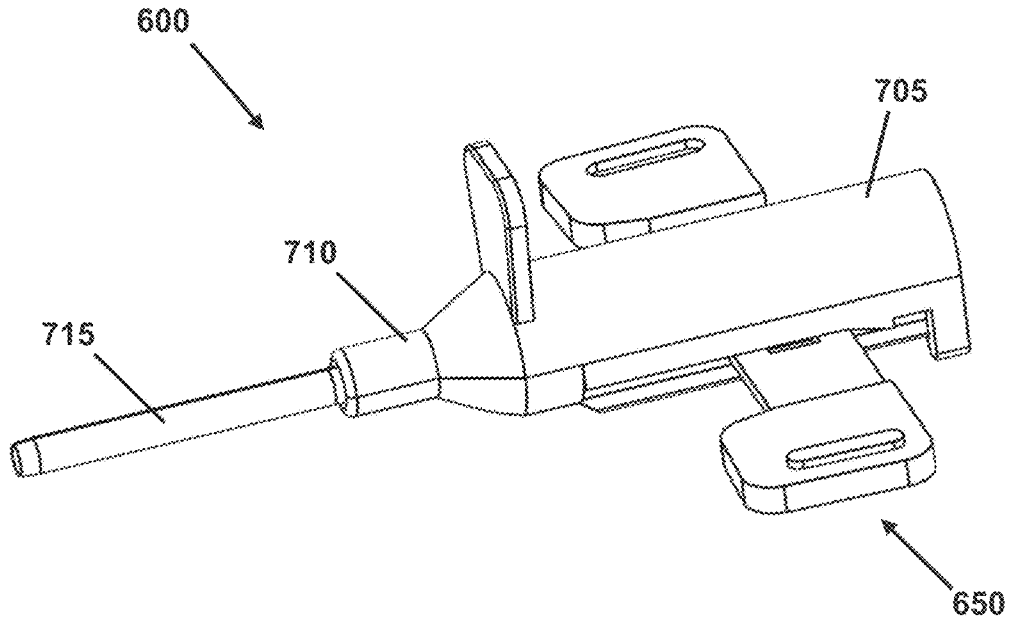
FIG. 12A is a perspective view of the exemplary catheter device of FIG. 11A, with the catheter portion of the device residing in a partially extended position.
Figure 12B:
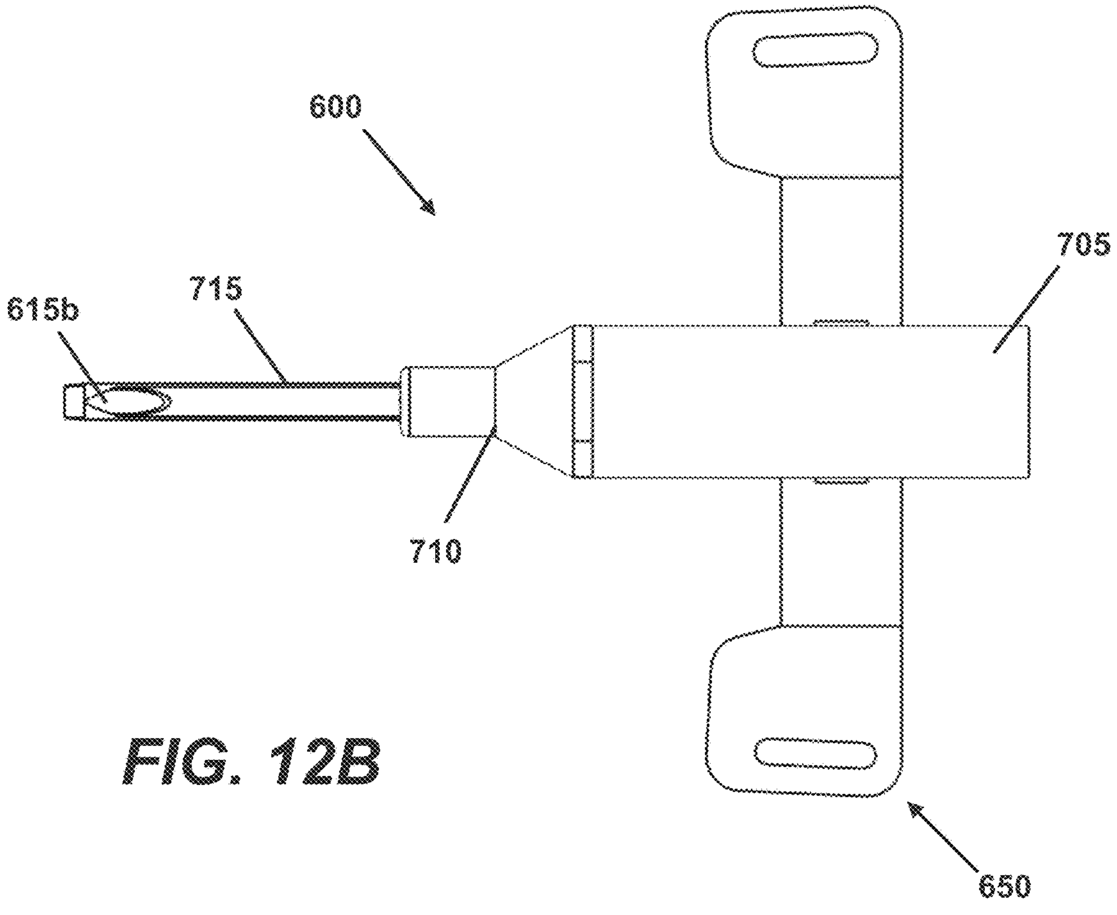
FIG. 12B is a top view of the catheter device shown in FIG. 12A, with a catheter of the device shown in partial transparency.
Figure 12C:
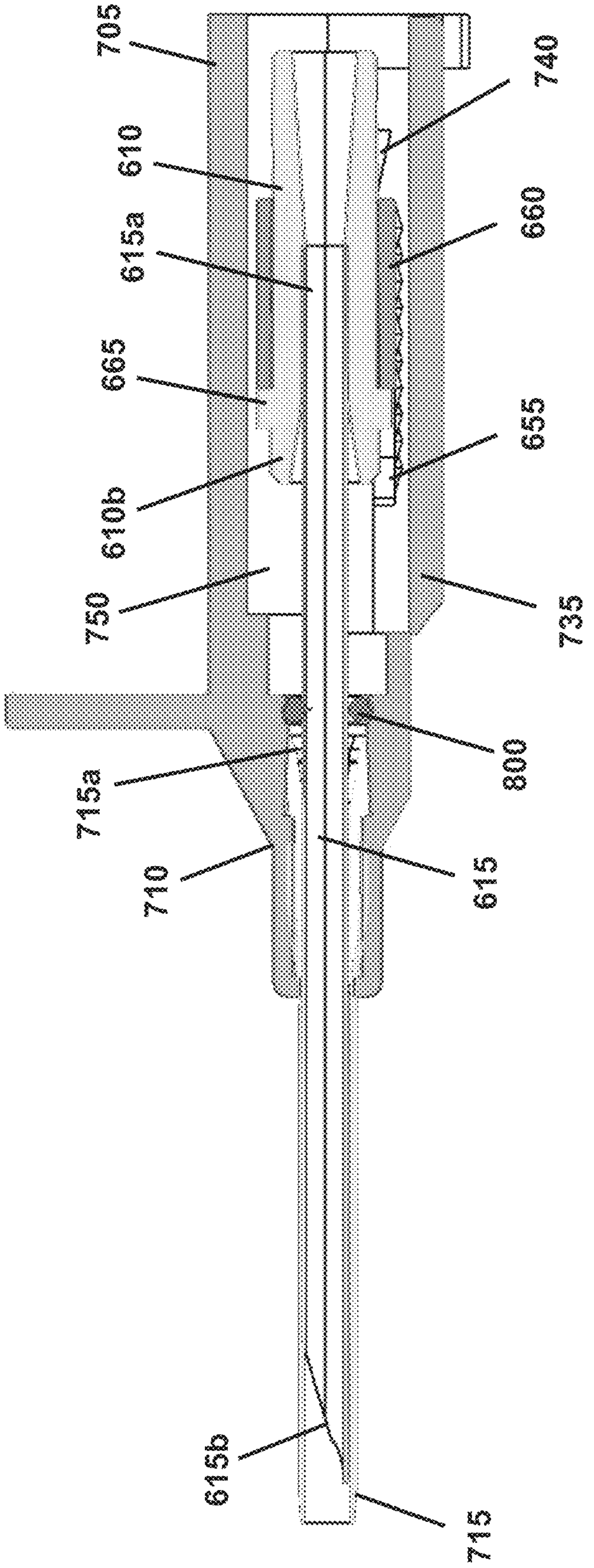
FIG. 12C is an enlarged cross-sectional side view of the catheter device shown in FIG. 12A.
Figure 13A:
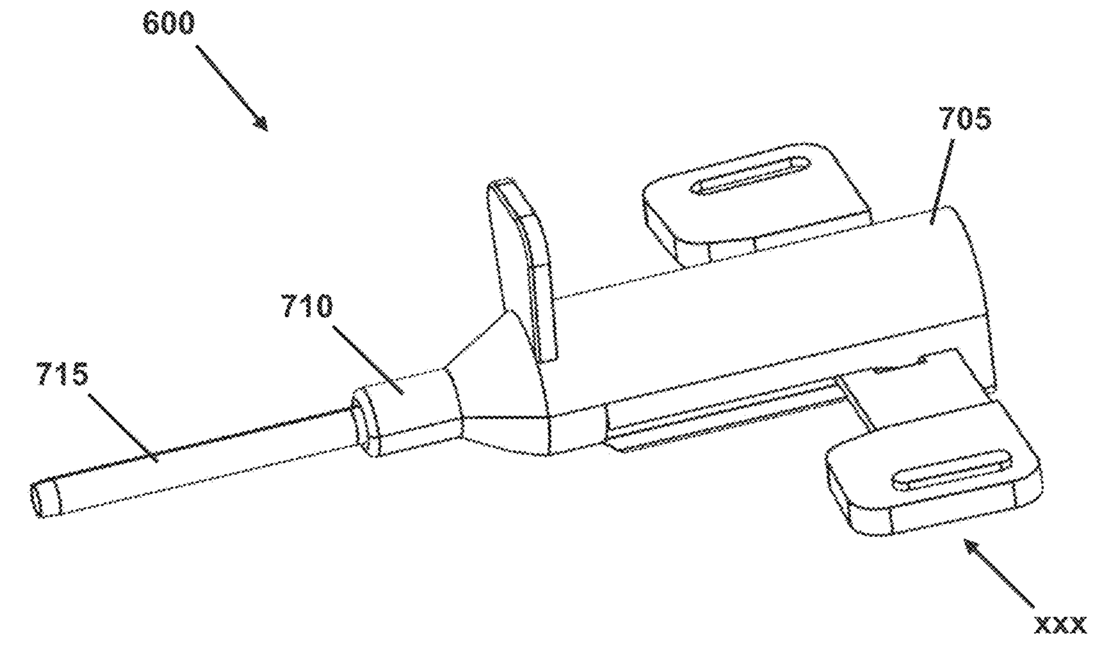
FIG. 13A is a perspective view of the exemplary catheter device of FIG. 11A, with the catheter portion of the device residing in a fully extended position.
Figure 13B:
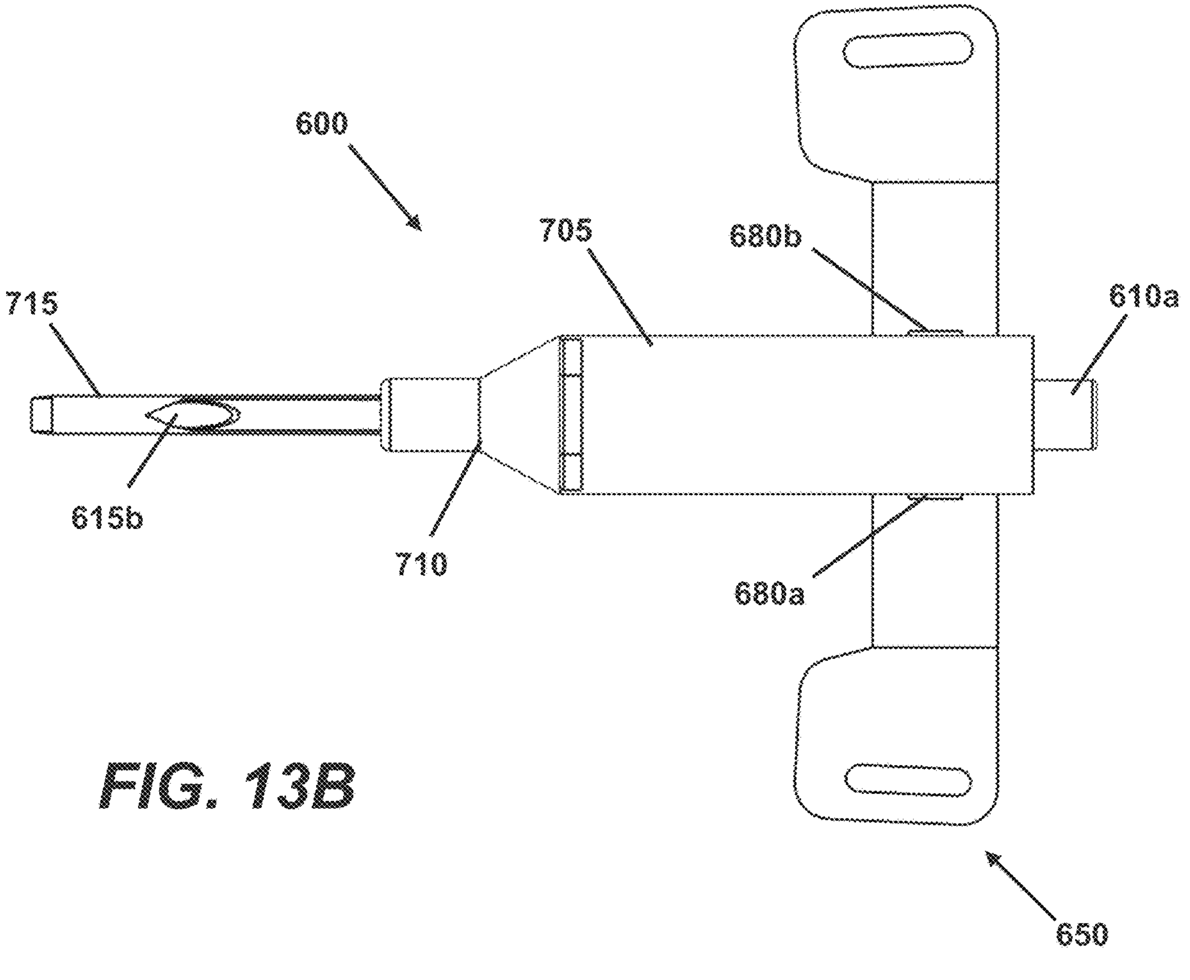
FIG. 13B is a top view of the catheter device shown in FIG. 13A.
Figure 13C:
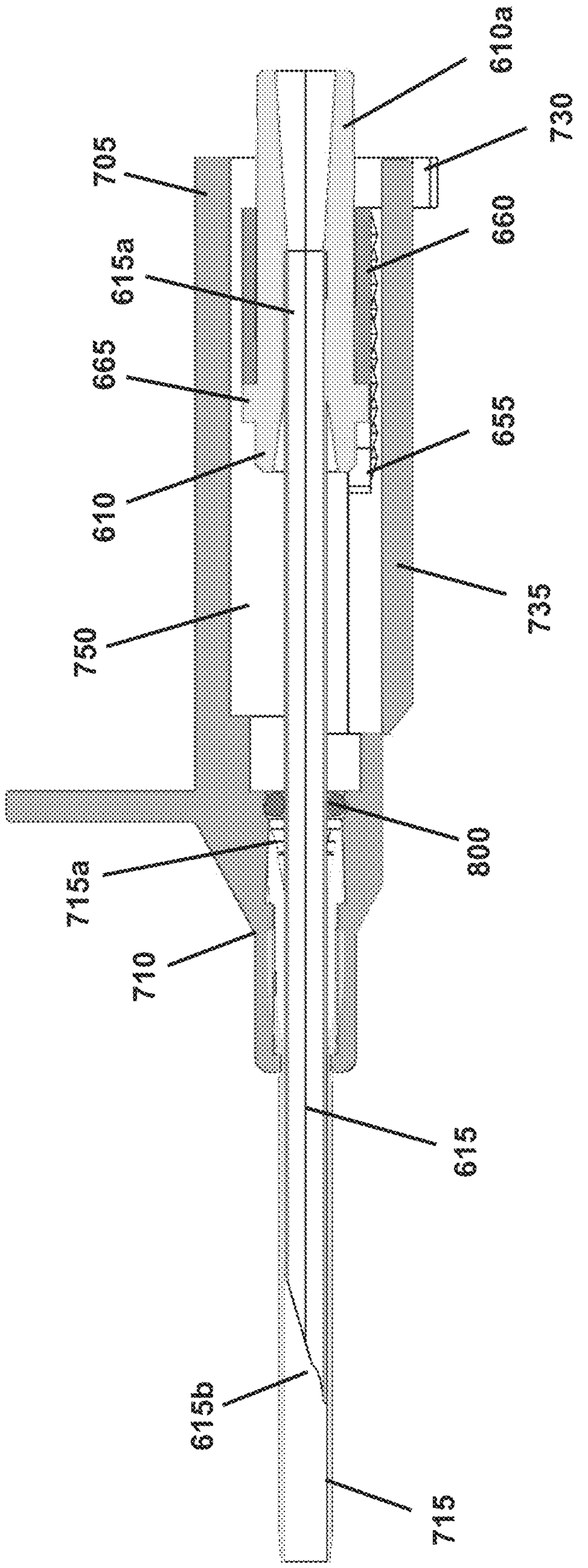
FIG. 13C is an enlarged cross-sectional side view of the catheter device shown in FIG. 13A.
Figure 14:
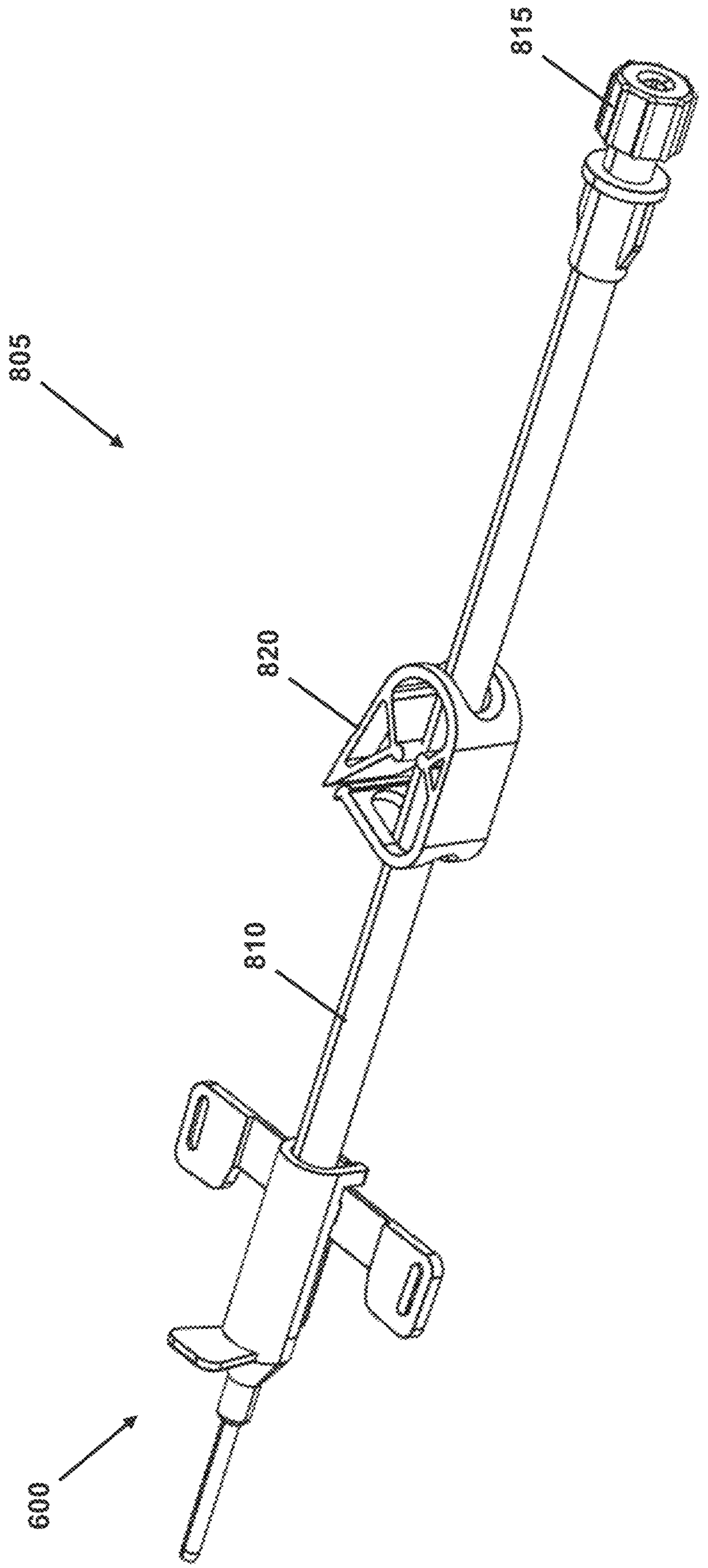
FIG. 14 depicts one exemplary embodiment of a vascular access catheter device assembly utilizing an exemplary embodiment of a vascular access catheter device as shown in FIGS. 11A-13C.

Further details regarding the exemplary needle portion 605 of the device 600 may be observed by referring to FIGS. 9A-9B and the cross-sectional views of FIGS. 11C, 12C and 13C. As shown therein, the exemplary needle hub 610 is generally elongate and includes a through-bore that imparts a substantially hollow construction to the needle hub. The needle hub 610 is dimensioned to fit within a hollow receiving cavity 750 in the body 705 of the catheter portion 700. The bore through the needle hub 610 forms a pathway for blood flow when the device 600 is in use.

The needle 615 of the needle portion 605 has a proximal end 615*a* thereof that is inserted into the bore in the needle hub 610 at a distal end 610*b* thereof. An internal diameter dimension of the bore in the needle hub 610 and an outside diameter dimension of the proximal end of the needle 615 may be selected so that the proximal end of the needle is securely retained in the needle hub such as by a press fit or a similar interaction between the components. In other embodiments, retention of the needle in the needle hub may be accomplished with adhesive, or by any other technique understood by those of skill in the art. Other techniques for coupling the needle to the needle hub may also be used, the only limitation being that the needle and needle hub move together in a sliding fashion relative to the catheter portion of a given device.

A distal, free end, of the needle 615 is provided with a sharp point 615*b* for the purpose of piercing the skin of a patient and subsequently accessing the patient's fistula/graft or a peripheral vessel. The specific needle gauge, needle construction, etc., may vary in keeping with accepted practices understood in the art.

In this exemplary embodiment of the device 600, a gripping and actuating component 650 is coupled to the needle hub 610, and moves with the needle hub relative to the catheter portion 700 of the device. As described in more detail below, the gripping and actuating component 650 helps to facilitate movement of the needle portion 605 during use of the device 600.

The exemplary gripping and actuating component 650 used herein includes a pair of wing-like gripping portions 655 that extend in opposite and substantially transverse directions from a central connecting element 660. While the gripping portions 655 of the gripping and actuating component 650 are provided with the illustrated wing-like shape to facilitate gripping and manipulation of the device 600 by a user, as well as taping of the device to a limb of a patient after fistula/graft or peripheral vessel access, the gripping portions of alternative embodiments may employ other shapes.

The central connecting element 660 of the gripping and actuating component 650 is a substantially cylindrical component having an axial through-bore of a diameter that can receive the needle hub 610. More particularly, the outside diameter of at least a portion of the needle hub 610 and the diameter of the through-bore in the central connecting element 660 are preferably selected to produce a tight fit that is sufficient to retain the central connecting element on the needle hub in the course of ordinary use of the device 600. In other embodiments, however, retention of the central connecting element 660 on the needle hub 610 may instead be accomplished with adhesive, by plastic welding, or by any other technique understood by those of skill in the art. In still other exemplary embodiments, the needle hub 605 and the gripping and actuating component 650 may be one unitary structure instead of separate components. For example, the needle hub 605 and the gripping and actuating component 650 may be a singular molded component, with the gripping elements extending in transverse opposite directions from a central area thereof.

In this exemplary embodiment of the device 600, a hard stop 665 may be located on the exterior of the needle hub 610 to help properly locate the central connecting element 660 of the gripping and actuating component 650. The exemplary hard stop 665 is comprised of a shoulder that extends outward from the outer surface of the needle hub 610. The outer diameter of the hard stop (shoulder) 665 may be, but is not required to be, the same as the outer diameter of the central connecting element 660 of the gripping and actuating component 650. When present in other embodiments, the hard stop may be a tab or another element that does not encircle the needle hub, but against which the central connecting element of the gripping and actuating component may nonetheless abut.

A needle portion position locking slot 680*a*, 680*b* (only slot 680*a* visible in FIGS. 9A-9B) is also present in each of the wing-like gripping portions 655 of this exemplary gripping and actuating component 650, the purpose of which is described in more detail below. A single one of such slots may be present on a gripping portion of other exemplary device embodiments.

The wing-like gripping portions 655 of the gripping and actuating component 650 are preferably bendable to facilitate grasping and manipulating of the device 600 during use. For example, and without limitation, each of the wing-like gripping portions 655 may preferably be bent at least upward (relative to the orientation of the device during normal use) and also toward each other. In this example, the wing-like gripping portions 655 are sufficiently bendable such that the outward, upper faces 670*a*, 670*b* thereof may be placed into abutting contact and held between the thumb and index (or other) finger(s) of a user during, for example, the process of inserting the needle 615 of the device 600 into a patient.

One of a cooperating pair of releasable engagement features 675*a*, 675*b* may be located in each of the wing-like gripping portions 655 to aid in alignment and possible temporary retention of a bent and abutting position of the wing-like gripping portions. In this exemplary embodiment, the releasable engagement features are provided in the form of a protruding tab 675*a* and a corresponding receiving slot 675*b*, but when present in other embodiments, such engagement features may take any functional form that would be understood by one of skill in the art.

Figure 10A:
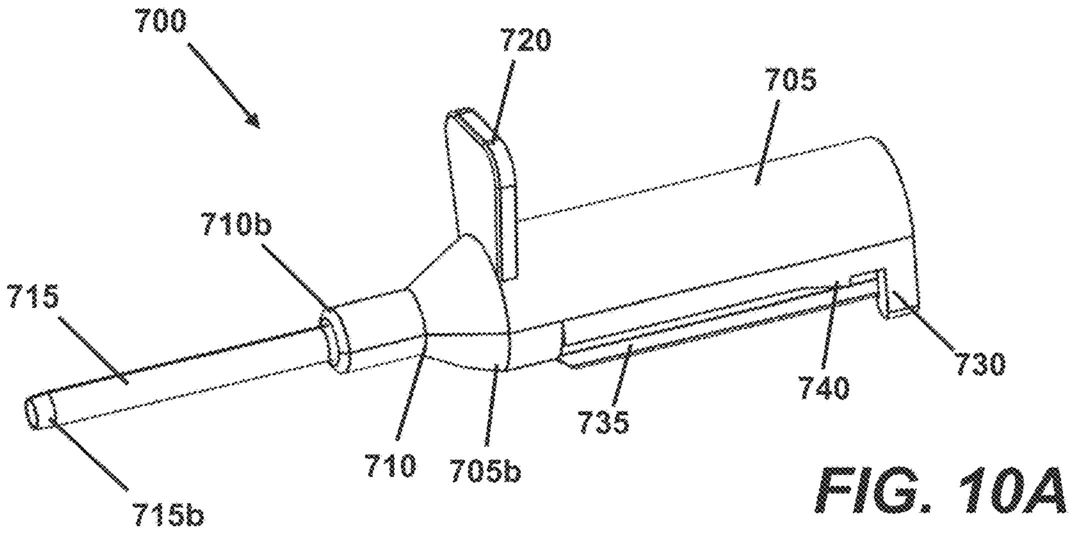
FIGS. 10A-10C are various perspective views of a catheter portion of an exemplary embodiment of a vascular access catheter device that also utilizes the needle portion of FIGS. 9A-9B.
Figure 10B:
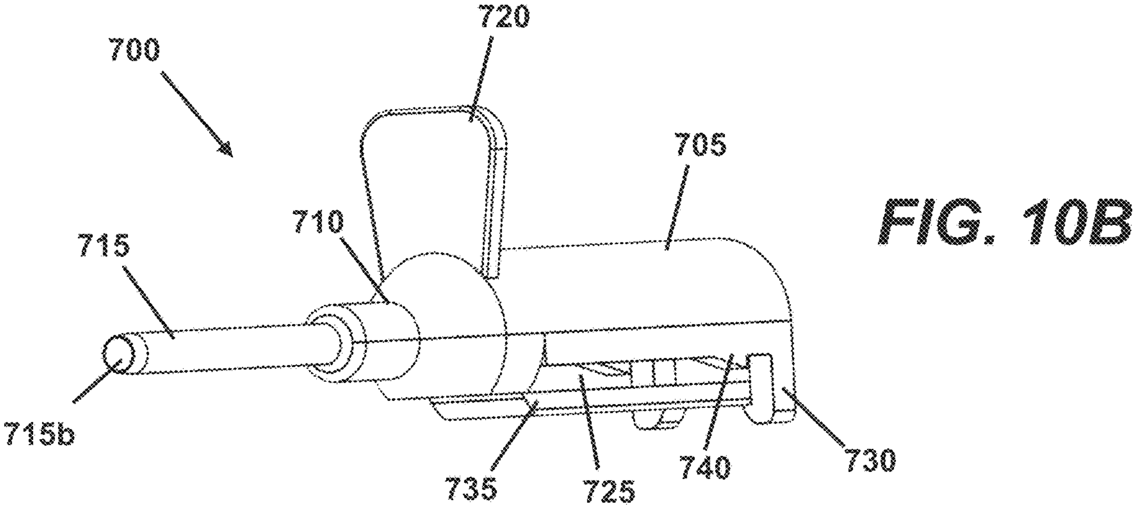
Figure 10C:
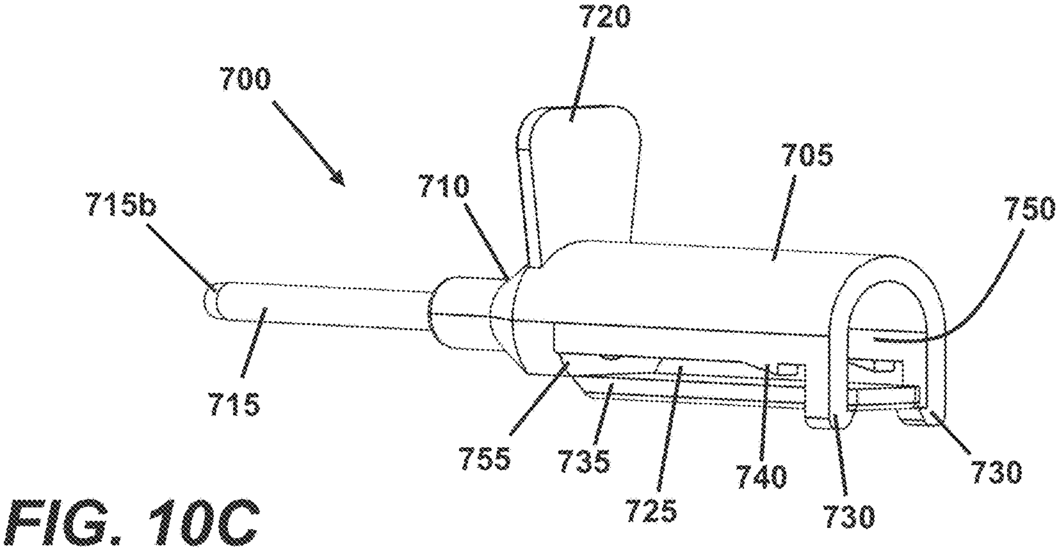

Further features of the catheter portion 700 of the device 600 may be observed by particular reference to FIGS. 10A-10C. As shown, the catheter portion 700 of the device 600 includes a body 705 of generally elongate and substantially hollow construction. The substantially open interior of the body 705 is dimensioned so as to permit uninterrupted sliding movement of the needle hub 610.

A distal end 705*b* of the body 705 forms a catheter hub 710 that extends axially in a proximal-to distal direction and which, in this exemplary embodiment, includes a distal end of reduced diameter and a tapered portion that connects the distal end to the body. A hollow catheter 715, having an open distal end 715*b* and a proximal end 715*a* (see, e.g., FIG. 11C) designed for retention within the catheter hub 710, extends axially from the distal end of the catheter hub in a proximal-to distal direction.

The proximal end 715*a* of the catheter 715 may be retained in the catheter hub 710 by any of the needle retention techniques mentioned above or by any other acceptable technique known to one of skill in the art. In other embodiments, the catheter 715 may be an integrally molded part of the catheter hub 710. The free, distal end 715*b* of the catheter 715 may be tapered and/or may include any other features that may facilitate entry of the distal end of the catheter into the fistula/graft or peripheral vessel of a patient subsequent to initial access by the needle 615, and/or may facilitate blood flow during a hemodialysis or other vascular access procedure. Along with the needle 615, the specific construction of the catheter 715 may vary in keeping with accepted practices understood in the art. For example, the catheter 715 may be constructed from a fluoroplastic material.

The exemplary body 705 of this exemplary device 600 embodiment also includes a grip 720 or similar feature that extends from the body to facilitate sliding or retention of the catheter portion 700 by a user of the device. A pair of needle portion position locking tabs 740 are also present on opposite sides of the body 705, the purpose of which is described in more detail below. A single one of such tabs may be present on the body of other exemplary device embodiments.

This exemplary embodiment of the body 705 further includes an opening that is provided to accommodate the wing-like gripping portions 655 of the gripping and actuating component 650 associated with the needle portion 605, and sliding movement thereof, when the needle portion and the associated gripping and actuating component are assembled to the catheter portion 700. In this exemplary embodiment, the opening is comprised of a pair of slots 725 (see FIGS. 10B-10C) that pass through opposite walls of the body 705. The body 705 may further include a hard stop(s) 730 that sets the limit of travel of the needle portion 605 toward the proximal end of the body 705.

The slot 725 resides above a bottom section, or gripping and actuating component support wall 735 of the body 705. The gripping and actuating component support wall 735 of the body 705 helps to retain and guide the gripping and actuating component 650 of the needle portion 605 during use of the device 600. In this exemplary embodiment of the device, the gripping and actuating component support wall 735 is an independent (separate) element that is coupled to and retained on the body 705. In other embodiments, the gripping and actuating component support wall may be an integral (e.g., molded) portion of the body as long as the needle portion 605 can be properly assembled to the catheter portion 700.

Reference to the assembled device views of FIGS. 11A-13C, and particularly to the cross-sectional views of FIGS. 11C, 12C and 13C, reveals a more thorough understanding of the construction and operation of the exemplary vascular access catheter device 600.

FIGS. 11A-11C illustrate the exemplary device 600 with the needle portion 605 in a fully extended position relative to the catheter portion 700, which results in the needle tip 615*b* and perhaps some additional length of the needle 615 protruding from the open distal end of the catheter 715. This is the proper position in which the catheter portion 700 should reside during initial piercing of a patient's skin and accessing of the underlying fistula/graft or peripheral vessel using the needle 615 of the device 600.

Referring now specifically to FIG. 11C, it may be observed that the catheter 715 is installed into the body 705, with the proximal end of the catheter secured within the bore of the catheter hub 710. Likewise, the needle portion 605, with the gripping and actuating component 650 coupled thereto, is installed in the catheter portion 700 with the needle hub 610 of the needle portion arranged in the open interior of the body 705 and the needle 615 extending through the catheter 715. This assembled arrangement of the needle portion 605 and the catheter portion 700 allows for slidable movement of the needle portion relative to the catheter portion, and vice versa. The limit of slidable (extending) movement of the needle portion 605 toward the distal end of the catheter portion 700 in this exemplary device embodiment, occurs at the point of contact between forward edges of the gripping portions 655 of the gripping and actuating component 650 and a rear face of a lower wall 755 of the body 705 that resides rearward of the catheter hub 710. As should be apparent, a different hard stop(s) to extending movement of the needle portion 605 may instead be provided.

The inside diameter of the catheter 715 is preferably similar in dimension to the outside diameter of the needle 615, so as to produce a close-tolerance but sliding fit between the catheter and the needle after the needle portion 605 and the catheter portion 700 of the device 600 are assembled to one another. Nonetheless, a seal 800, such as without limitation, an O-ring, may be placed at or near the meeting point of the bore in the catheter hub 710 and the open interior of the of the catheter portion body 705 to prevent possible blood leakage between the needle 615 and the catheter 715 during use of the device 600.

From the foregoing description and a review of corresponding FIGS. 11A-11C, it should be understood that when the needle portion and the catheter portion 700 are properly assembled, as explained above, the needle 615 is substantially concentrically located within the catheter 715, and the body 705 and attached catheter 715 are together linearly slidable relative to the needle hub 610 and the attached needle 615, and vice versa. For example, the body 705 and attached catheter 715 may be slidably displaced relative to the needle hub 610 and needle 615 by maintaining the position of the needle portion 605 using the gripping and actuating component 650 and using the grip 720 on the body 705 to slide the catheter portion 700 relative to the needle portion. Likewise, the needle hub 610 and needle 615 may be slidably displaced relative to the body 705 and attached catheter 715 by maintaining the position of the body and using the gripping and actuating component 650 to slide the needle portion 605 relative to the catheter portion 700.

As mentioned above, the position of the device 600 illustrated in FIGS. 11A-11C, with the needle 615 protruding from the distal end of the catheter 715, is the position of the device to be used to initially pierce a patient's fistula/graft or peripheral vessel with the needle tip 615*b*. It should also be understood that when the device is used in this position as described, the distal end of the catheter 715 will follow the needle 615 into the fistula/graft or peripheral vessel.

Once the needle 615 and a sufficient length of the catheter 715 have been initially placed in the fistula/graft or peripheral vessel, the needle portion 600 may be moved to an intermediate position relative to the catheter portion, as shown in FIGS. 12A-12C, or may be moved directly to a final position relative to the catheter portion, as shown in FIGS. 13A-13C.

As illustrated in FIGS. 12A-12C, once blood flash is seen in a length of blood transfer tubing that is normally attached to the proximal end 610*a* of the needle hub 610 (see, e.g., tubing 810 in FIG. 14), it may be desirable in some cases to partially retract the needle portion 605 in a distal-to-proximal direction relative to the catheter portion 700 to resultantly achieve optimum blood flow and position. This partially retracted position of the needle portion 605 relative to the catheter portion 700 is referred to generally herein as a "parked" position. The positional relationship of the catheter 715 and the needle 615 may also be further adjusted if needed to maintain an optimized blood flow.

As indicted in FIGS. 13A-13C, either subsequent to "parking" the needle portion 605, or directly after initial insertion of the needle 615 and catheter if acceptable blood flow is achieved without employing a "parking" step, the needle portion is fully retracted relative to the catheter portion 700. Full retraction of the needle portion 605 occurs in this exemplary embodiment at the point of contact between rear faces/edges of the gripping portions 655 of the gripping and actuating component 650 and forward faces/edges of the hard stops 730 on the body 705 of the catheter portion 700. The needle portion 605 cannot be moved any farther toward the proximal end of the body 705 during normal use of the assembled device 600. The fully retracted position of the needle portion 605 may be indicated by an audible click or other sound.

In the fully retracted position, a returning (i.e., proximal-to-distal) movement of the needle portion 605 toward the previously described "parked" position (FIGS. 12A-12C) or extended position (FIGS. 11A-11C) is preferably prevented by means of a needle portion locking mechanism. The needle portion locking mechanism is comprised of and operates via engaging interaction of the needle portion position locking tabs 740 on the body 705 of the catheter portion 700 and the needle portion position locking slots 680*a*, 680*b* on the gripping portions 655 of the gripping and actuating component 650. Particularly, and as best illustrated in FIG. 13C, when the needle portion 605 is placed in the fully retracted position, the needle portion position locking tabs 740 on the body 705 enter the needle portion position locking slots 680*a*, 680*b* on the gripping portions 655 of the gripping and actuating component 650. Entry of the locking tabs 740 into the locking slots 680*a*, 680*b* may produce the audible locked position-indicating click or other sound mentioned above.

In this embodiment of the device 600, sliding movement of the needle portion 605 relative to the catheter portion 700 (or vice versa) is no longer possible after the needle portion position locking tabs 740 on the body 705 become engaged with the needle portion position locking slots 680*a*, 680*b* on the gripping portions 655. Rather, the needle portion locking mechanism causes the device 600 to become permanently locked in the fully retracted position which, because the needle tip is covered by the catheter, prevents possible needle stick injuries to health care workers or other users upon removal of the device from the patient and subsequent disposal of the device.

While the exemplary embodiment of the device 600 described and shown herein includes a needle portion locking mechanism that causes the device 600 to become permanently locked in the fully retracted position, it should be apparent to one of skill in the art that it is also possible, if desired, to provide an exemplary vascular access catheter device with a releasable needle portion locking mechanism. For example, an exemplary device may be provided with needle portion position locking tabs and cooperating needle portion position locking slots whose engagement is sufficient to generally prevent unintended movement of the needle portion toward its extended position during normal use, while nonetheless allowing for deliberate disengagement of the needle portion locking mechanism via a user-applied sliding force of abnormally high magnitude on the needle portion or the catheter portion of the device.

With the needle portion 605 and needle 615 of the exemplary device 600 locked in the fully retracted position and the catheter 715 properly located in the fistula/graft or peripheral vessel of the patient, the catheter device 600 may be secured to the limb of the patient using tape or another technique known in the art.

As should be readily obvious to one of skill in the art, placing the catheter 715 of the exemplary catheter device 600 into a fistula/graft or a peripheral vessel and over the needle tip 615*b* as described above serves to prevent the needle tip from damaging the fistula/graft or peripheral vessel and also, therefore, prevents infiltration and related hematoma problems. And unlike known devices, the needle 615 of the exemplary catheter device 600 remains largely within the catheter 715 during a hemodialysis or other vascular procedure, thereby substantially eliminating any chance that the catheter may collapse, kink, etc., and interfere with blood flow or cause damage on its own.

As described above, therefore, the needle portion 605 has an extended position where the needle tip 615*b* extends beyond the catheter 715 and the catheter is thereby kept from interfering with initial use of the needle 615 to access the fistula/graft or peripheral vessel of a patient. Likewise, the needle portion 605 has a retracted position where the needle 615 is drawn into the catheter 715 and out of the fistula/graft or peripheral vessel while the catheter itself remains inserted therein, which prevents the needle/needle tip from causing damage to the fistula/graft or peripheral vessel. Consequently, in addition to securing the overall catheter device 600 to the patient, it is also preferable to provide a mechanism, such as the exemplary needle portion locking mechanism described above, whereby it can be ensured that the position of the needle portion 605 relative to the position of the catheter portion 700 will be maintained after the needle 615 has been fully retracted.

To guard against inadvertent contact with the sharp tip 615*b* of the needle 615 when the needle is in an extended position, a protective device, such as but not limited to a cap may be associated with the needle. When a cap is used, the cap may be the same as or similar to the cap shown in FIGS. 3A-3B. Any of the cap retention techniques mentioned herein may be employed in such an embodiment.

One exemplary embodiment of a vascular access catheter device assembly 805 utilizing the exemplary vascular access catheter device 600 described above, is illustrated in FIG. 14. As shown, a length of blood transfer tubing 810 is connected at one end to the proximal end 610*a* of the needle hub 605. The proximal end 610*a* of the needle hub 605 may have a barbed profile or may otherwise be adapted to facilitate connection of such tubing. A stopper element 815 is located at the opposite end of the tubing 810, and in between the exemplary vascular access catheter device 600 and the stopper element resides a clamp 820. The exemplary assembly 805 is provided for purposes of illustration, not limitation, and one of skill in the art would understand that there are numerous possible variations of a vascular access catheter device assembly employing the exemplary vascular access catheter device 600.

Various exemplary vascular access catheter device embodiments have been described and shown herein for purposes of illustration. Other variations are also possible. For example, and without limitation, the catheter hub and needle hub of an exemplary vascular access catheter device, may be manufactured from a transparent or semi-transparent material to permit viewing of the flow of blood passing through the device during use.

As used herein, the term "distal" is intended to refer to the end of the catheter device where the needle normally resides, and the term "proximal" is intended to refer to the end of the catheter device where fluid transport tubing is normally connected.

As used herein, the terms "axial" or "axially" are intended to refer to a direction that is parallel to the length-wise axis of the element/component to which the term is being applied.

As used herein, the term "central axis" is intended to refer to the symmetrical axis of a component or the device, and the term "central bore" is intended to refer to a bore that is symmetrical about the central axis.

As used herein "first" and "second" are intended only to differentiate between two elements or components for purposes of description, and not to indicate an order, a preference, or superiority or inferiority, of any kind.

As used herein, the term "irreversible" is intended to mean not able to be reversed under normal operation or when subjected to normal operating forces, and does not necessarily require that reversal is impossible under other conditions.

As used herein, the term "prohibit" is intended to mean prevent or make impossible under normal operation or when subjected to normal operating forces, and does not necessarily require that prohibition is impossible under other conditions.

While certain embodiments of the inventive concept are described in detail above, the scope of the inventive concept is not considered limited by such disclosure, and modifications are possible without departing from the spirit of the inventive concept as evidenced by the following claims:

What is claimed is:

1. A vascular access catheter device with an inline needle, comprising:

a catheter portion having a hollow body with a catheter hub that extends from a distal end thereof, and a hollow catheter that extends from a distal end of the catheter hub; and a needle portion having a hollow needle hub, a hollow needle that extends from a distal end of the needle hub, and a gripping and actuating component having a pair of extending gripping portions, the needle hub arranged and maintained within the body of the catheter portion such that at least a portion of the needle is located in the catheter and the gripping portions of the gripping and actuating component extend outward in opposite directions through openings in the body of the catheter portion;

wherein the needle portion is selectively linearly displaceable relative to the catheter portion between an extended position where at least a tip of the needle protrudes from the catheter, and a retracted position where the needle is covered by the catheter.

2. The vascular access catheter device of claim 1, wherein a proximal end of the needle hub is configured for the connection of hemodialysis or other fluid transport tubing.

3. The vascular access catheter device of claim 1, wherein contact between the gripping portions of the gripping and actuating component and a wall of the body of the catheter portion determines a fully extended position of the needle portion relative to the catheter portion.

4. The vascular access catheter device of claim 1, wherein contact between the gripping portions of the gripping and actuating component and a hard stop near a proximal end of the body of the catheter portion determines a fully retracted position of the needle portion relative to the catheter portion.

5. The vascular access catheter device of claim 1, further comprising a needle portion retracted position locking mechanism that retains the needle portion in the retracted position, the needle portion retracted position locking mechanism comprising:

at least one downwardly extending needle portion retracted position locking tab on the body of the catheter portion; and at least one cooperating needle portion retracted position locking slot on at least one of the gripping portions of the gripping and actuating component;

wherein the at least one needle portion retracted position locking tab will become engaged with the at least one cooperating needle portion retracted position locking slot when the needle portion is placed in the retracted position.

6. The vascular access catheter device of claim 1, wherein the gripping portions of the gripping and actuating component are bendable.

7. The vascular access catheter device of claim 6, wherein the gripping portions of the gripping and actuating component are bendable in at least an upward direction relative to the orientation of the catheter device during normal use, and also toward each other, such that outward upper faces of the gripping portions are placeable into abutting contact.

8. The vascular access catheter device of claim 1, wherein the gripping and actuating component includes a central connecting element that encircles the needle hub, and the gripping portions extend in opposite and substantially transverse directions therefrom.

9. The vascular access catheter device of claim 1, wherein the gripping and actuating component is a separate component that is attached to the needle hub of the needle portion.

10. The vascular access catheter device of claim 1, wherein a proximal end of the needle is retained in a bore in the needle hub.

11. The vascular access catheter device of claim 1, wherein a proximal end of the catheter is retained in a bore in the catheter hub.

12. The vascular access catheter device of claim 1, further comprising a seal between the needle and the catheter to prevent the leakage of blood from the device during use.

13. The vascular access catheter device of claim 1, wherein the catheter and needle are insertable into the bloodstream of a patient without a break in an overall dialysis blood flow path.

14. The vascular access catheter device of claim 1, further comprising a support wall associated with the body of the catheter portion and below the openings therein, the support wall positioned and configured to support and guide the gripping and actuating component during sliding movement thereof.

15. A vascular access catheter device with an inline needle, comprising:

a catheter portion having an elongate hollow body with a catheter hub that extends from a distal end thereof, and a hollow catheter that extends from a distal end of the catheter hub;

a pair of axially-oriented slots located through opposite walls of the body of the catheter portion;

a needle portion having an elongate and hollow needle hub with a proximal end configured for the connection of fluid transport tubing, and a hollow needle that extends from a distal end of the needle hub;

a gripping and actuating component coupled to the needle hub by a central connecting element, the gripping and actuating component having a pair of bendable gripping portions that extend in opposite and substantially transverse directions from the central connecting element; and a seal between the needle and the catheter;

wherein at least the distal end of the needle hub is arranged and maintained within the body of the catheter portion such that at least a portion of the needle is located in the catheter, and the gripping portions of the gripping and actuating component extend through respective ones of the slots in the body of the catheter portion; and wherein the needle portion and the gripping and actuating component coupled thereto are selectively linearly displaceable as a single unit relative to the catheter portion, between an extended position where at least a tip of the needle of the needle portion protrudes from the catheter of the catheter portion, and a retracted position where the needle of the needle portion is covered by the catheter of the catheter portion.

16. The vascular access catheter device of claim 15, wherein:

a proximal end of the needle is retained in a bore in the needle hub; and a proximal end of the catheter is retained in a bore in the catheter hub.

17. The vascular access catheter device of claim 15, wherein:

contact between forward edges of the gripping portions of the gripping and actuating component and a wall of the body of the catheter portion determines a fully extended position of the needle portion relative to the catheter portion; and contact between rearward edges of the gripping portions of the gripping and actuating component and a hard stop near a proximal end of the body of the catheter portion determines a fully retracted position of the needle portion relative to the catheter portion.

18. The vascular access catheter device of claim 15, further comprising a needle portion retracted position locking mechanism that retains the needle portion in the retracted position, the needle portion retracted position locking mechanism comprising:

at least one downwardly extending needle portion retracted position locking tab on the body of the catheter portion; and at least one cooperating needle portion retracted position locking slot on at least one of the gripping portions of the gripping and actuating component;

wherein the at least one needle portion retracted position locking tab will become engaged with the at least one cooperating needle portion retracted position locking slot when the needle portion is placed in the retracted position.

19. A method of safely performing a blood transfer procedure on a patient without a break in an overall blood flow path, comprising:

(a) providing an arteriovenous catheter device with an inline needle, the arteriovenous catheter device comprising:

a catheter portion having a hollow body with a catheter hub that extends from a distal end thereof, and a hollow catheter that extends from a distal end of the catheter hub and terminates in a free and open distal end;

longitudinally-oriented slots through opposite walls of the body of the catheter portion;

a needle portion having a hollow needle hub, a hollow needle that extends from a distal end of the needle hub and terminates in a needle tip, and a gripping and actuating component having a pair of extending gripping portions, the needle hub arranged and maintained within the body of the catheter portion such that at least a portion of the needle is located in the catheter and the gripping portions of the gripping and actuating component extend outward in opposite directions through openings in the body of the catheter portion, and the needle portion is selectively linearly displaceable relative to the catheter portion between an extended position where at least a tip of the needle protrudes from the catheter, and a retracted position where the needle is covered by the catheter;

a needle portion retracted position locking mechanism configured to retain the needle portion in a fully retracted position; and fluid transfer tubing connected at one end to a proximal end of the needle hub and at an opposite end to a blood collection vessel or a hemodialysis machine;

(b) with the needle portion of the arteriovenous catheter device in the extended position, piercing the skin of the patient with the tip of the arteriovenous catheter device needle and thereafter inserting the needle and the distal end of the catheter into an underlying fistula/graft or peripheral vessel to initiate blood flow through the arteriovenous catheter device;

(c) retracting the needle portion thereof to the fully retracted position while a portion of the catheter remains in the fistula/graft or peripheral vessel of the patient; and (d) releasably securing the arteriovenous catheter device to the patient.

20. The method of claim 19, further comprising the step of retracting the needle portion of the arteriovenous catheter device to an intermediate retracted position and adjusting the position of the catheter of the arteriovenous device within the fistula/graft or peripheral vessel of the patient to optimize blood flow before retracting the needle portion of the arteriovenous catheter device to the fully retracted position.

* * * * *